US007098039B1

(12) United States Patent
Lloyd et al.

(10) Patent No.: US 7,098,039 B1
(45) Date of Patent: Aug. 29, 2006

(54) ANALYSIS OF A SAMPLE TO DETERMINE ITS CHARACTERISTIC CYCLE TIME

(75) Inventors: Christopher J. Lloyd, Manchester (GB); David J. Clarke, Sandbach (GB)

(73) Assignee: The Victoria University of Manchester, Manchester (GB)

( * ) Notice: Subject to any disclaimer, the term of this patent is extended or adjusted under 35 U.S.C. 154(b) by 0 days.

(21) Appl. No.: 09/743,195

(22) PCT Filed: Jul. 8, 1999

(86) PCT No.: PCT/GB99/02047

§ 371 (c)(1),
(2), (4) Date: Mar. 1, 2001

(87) PCT Pub. No.: WO00/03247

PCT Pub. Date: Jan. 20, 2000

(30) Foreign Application Priority Data

| Jul. 8, 1998 | (GB) | ................................. | 9814715.0 |
| Dec. 19, 1998 | (GB) | ................................. | 9827903.7 |
| Dec. 19, 1998 | (GB) | ................................. | 9827910.2 |

(51) Int. Cl.
*G01N 21/76* (2006.01)
*G01N 21/64* (2006.01)
*F21V 9/16* (2006.01)
*G01J 3/443* (2006.01)

(52) U.S. Cl. .................. 436/172; 250/459.1; 356/317; 422/82.07

(58) Field of Classification Search ............... 436/172; 250/459.1; 356/317; 422/82.07
See application file for complete search history.

(56) References Cited

U.S. PATENT DOCUMENTS

| 4,421,860 A | | 12/1983 | Elings et al. |
| 5,254,477 A | * | 10/1993 | Walt ........................... 436/172 |
| 5,631,169 A | * | 5/1997 | Lakowicz et al. .......... 436/537 |

FOREIGN PATENT DOCUMENTS

| WO | WO94/18218 | 8/1994 |
| WO | WO96/27798 | 9/1996 |

OTHER PUBLICATIONS

Soper et al., Detection and identification of single molecules in solution, 1992, J. Opt. Soc. Am. B, vol. 9, No. 10, pp. 1761-1769.*
Patent Abstracts of Japan vol. 011, No. 137 (P-572), (May 1987) & JP61 277060 A (Joko: KK), (Dec. 1986).

* cited by examiner

Primary Examiner—Long V. Le
Assistant Examiner—Shafiqul Haq
(74) Attorney, Agent, or Firm—Nixon & Vanderhye P.C.

(57) ABSTRACT

An analysis for determining a characteristic cycle time of a sample. Active elements in the sample are excited with sufficient intensity and duration larger than the characteristic cycle time that at least some of the active elements are re-excited to an excited state substantially immediately following relaxation to a ground state, detecting quanta emitted by the active elements in the sample to obtain a detected signal, and analyzing the detected signal to derive the characteristic cycle time. The number of active elements in the sample and the intensity of the excitation are such that quanta are detected in a stream in which individual quanta are distinguishable from each other.

29 Claims, 11 Drawing Sheets

ANALYSIS OF A SAMPLE TO DETERMINE ITS CHARACTERISTIC CYCLE TIME

RELATED APPLICATIONS

This is a US national phase filing under 35 U.S.C. § 371 of PCT/GB 99/02047 filed Jul. 8, 1999 and claims priority from GB 90814715.0 filed Jul. 8, 1998, GB 9827903.7 filed Dec. 19, 1998 and GB 9827910.2 filed Dec. 19, 1998.

BACKGROUND

1. Technical Field

This invention relates to a method and apparatus for the analysis of a sample, and particularly though not exclusively to fluorescence analysis.

2. Related Art

Fluorescence analysis is an important experimental tool for both chemists and biologists, and is of particular interest to pharmaceutical researchers.

A known method of analysing fluorescence comprises exciting a sample of many hundreds of fluorophores with an intense pulse of light from a laser. The intensity of fluorescence emitted by the sample at a given delay following excitation is detected. The sample is excited again, and the intensity of fluorescence emitted by the sample at a different delay following excitation is detected. A series of measurements at various delays are made, and the fluorescence intensity is plotted as a function of the delay, to provide a distribution of fluorescence intensity over time. An upper state lifetime characteristic of the fluorophores comprising the sample may be derived from the gradient of the intensity distribution (for example, by fitting an exponential decay curve to the distribution).

Various other methods of measuring characteristic fluorophore lifetimes are known, and in each case the phase shift or demodulation of a detected signal compared to an excitation signal must be measured (see for example J R Lacowitz, Principles of Fluorescence Spectroscopy, Plenum Press, New York & London). However, present methods require comparatively lengthy averaging processes, which are unsuited to modern high speed processing of many measurements (for example in high throughput screening, or imaging).

A further limitation of the above method is that it requires a sample of many hundreds of fluorophores and high intensity illumination. A sample of the order of 100 fluorophores will not provide sufficient signal to noise to allow the measurement of fluorescence. The method cannot therefore be used to measure effects caused by a single fluorophore or a sample containing a small number of fluorophores or a sample that optically quenches rapidly. Furthermore, the method requires the use of pulsed laser sources and gated detectors to measure time domain fluorescence parameters such as decay rate.

A further known technique, known as number fluctuation spectroscopy may be used to determine the diffusion coefficients of particles in a fluid. Number fluctuation spectroscopy comprises illuminating a specified volume of fluid which particles will diffuse into and out of, and detecting light scattered by the particles when they are within the specified volume. An auto-correlation of the detected scattered light with itself will yield a characteristic frequency which is a function of the diffusion rate of the particles within the fluid. Number fluctuation spectroscopy may be used to determine a particle mean diffusion coefficient and thus may be used to determine a particle size.

WO96/27798 describes a technique known as fluorescence correlation spectroscopy, which may be considered to be a variant of number fluctuation spectroscopy. The technique is used when there are other scattering particles in the fluid which are not required to contribute to the detected signal. The particles of interest are made to fluoresce, and the fluorescent light is spectrally separated from the scattered light so that only the diffusion of the particles of interest is measured. Fluorescence correlation spectroscopy allows the determination of a diffusion coefficient, but does not provide the measurement of fluorescent lifetimes.

BRIEF SUMMARY

It is an object of the present invention to provide a method and apparatus for sample analysis which overcomes or mitigates the above disadvantages.

According to a first aspect of the invention there is provided a method of analysis for determining a characteristic cycle time of a sample, the method comprising exciting active elements in the sample with sufficient intensity that at least some of the active elements are re-excited to an excited state substantially immediately following relaxation to a ground state, detecting quanta emitted by the active elements in the sample to obtain a detected signal, and analysing the detected signal to derive the characteristic cycle time, wherein the number of active elements in the sample and the intensity of the excitation are such that quanta are detected in a stream in which individual quanta are distinguishable from each other.

The characteristic cycle time is defined as the time taken for an active element, to return to a ground state following excitation to an excited state. The term substantially immediately is intended to mean a period of time less than the time elapsed following excitation of the active element from the ground state until the active element returns to the ground state.

Suitably, the analysis of the detected signal includes correlating the detected signal with itself. Correlation in this context includes performing a Fourier transform, using a Fabry-Perot etalon, or any other suitable signal processing. For example, a signal stream containing at least 100 detected quanta is correlated with itself (auto-correlated) using the following equation:

$$G_{12}(u) = \Sigma N_1(t) N_1(t) N_2(t+\tau)$$

in order to determine frequencies within the signal stream.

The method may further include calibration to determine the average delay of the at least some active elements between relaxation to the ground state and subsequent re-excitation. This is not necessary when the excitation intensity is sufficient that the average delay is negligible.

The exemplary embodiment is advantageous because it maximizes the signal emitted by the active elements of the sample, since the active elements are made to cycle substantially continuously, and thereby provide a series of quanta (the active elements are effectively saturated). A measurement of a characteristic cycle time may be made very rapidly using the invention. For example, an experimental accuracy of 1% may be obtained in a period corresponding to less than $(100 \times$ the characteristic cycle time$)^2$. This compares to conventional fluorescence lifetime measurements where illumination is pulsed, and detectors are gated and must be reset for each of a series of measurements in order to measure a lifetime. For example, the prior art method known as time correlated single photon counting generally requires an experimental duration of a few minutes.

An important difference between the invention and the prior art is that the invention does not require the phase of the excitation to be measured. In prior art measurements of characteristic fluorescence lifetimes, a sample is excited using a pulse of illumination, and the time elapsed following the illumination until a fluorescence photon is emitted is measured. In order to do this the relative phase of the excitation and emission must be determined. This requires complicated and expensive high speed electronic circuits. In contrast to this, no information regarding the phase or timing of the excitation is required by the method according to the invention. The characteristic cycle time of a sample of fluorophores may be measured by monitoring the sample directly, and there is no need to monitor the excitation source.

The exemplary embodiment when used to measure a characteristic cycle time of a fluorophore using laser illumination, may appear superficially to resemble fluorescence correlation spectroscopy. However, there are several important differences between the invention and fluorescence correlation spectroscopy. Fluorescence correlation spectroscopy is used to determine diffusion coefficients of particles, and the detected experimental signal is caused by particles diffusing into and out of an illuminated area, the diffusion typically having a time scale of the order of milliseconds. The illumination is held at a low intensity to avoid quenching of fluorophores, and must be stabilized to a fixed intensity to avoid introducing experimental errors due to intensity fluctuations. In contrast to this the invention measures a characteristic lifetime of a sample of fluorophores by illuminating the sample at high intensity so that it cycles substantially continuously and emits a series of photons. A measurement of the characteristic lifetime, which is typically of the order of nanosecond, may be made for example to an accuracy of 1% over a time scale corresponding to less than $(100\times$ the characteristic lifetime$)^2$. Since the measurement may be made over such a small time duration, quenching of the sample, which will happen over a much longer duration, does not affect the measurement. Indeed, by making a series of measurements it may be possible to measure the effect of the quenching itself. There is no requirement to keep the intensity of the illumination stabilized to a particular value, provided that the intensity is sufficient to make the fluorophores of the sample cycle continuously.

Preferably, the method further comprises selecting the number of active elements and intensity of excitation so as to maximise the signal-to-noise ratio of the detected signal.

The detection of a quanta may be correlated with the detection of another property of the sample. The property may provide an analogue signal which is detected when it rises above a predetermined threshold. A detected signal may be auto-correlated, or cross-correlated against a test signal or digital mask, or may be correlated against a signal detected from a reference sample The characteristic cycle time of the sample may be modified by a suitable modification of the active elements' environment, by means which include chemical or physical means, and the modified characteristic cycle time is determined.

Suitably, at least some of the active elements have an excited level, an upper level of an emission transition and a lower level of the emission transition, and emit a detectable quanta upon relaxation from the upper level of the emission transition to the lower level of the emission transition, wherein the lifetime of the lower level of the emission transition or another energy level having a lesser energy than the lower level of the emission transition is influenced by the modification of the active elements' environment, and the effect of this is determined.

Suitably, at least some of the active elements are bound to a substrate by a member that permits vibrational motion of the active element wherein the lifetime of the lower level of the emission transition or another energy level having a lesser energy than the lower level of the emission transition, may be altered by modifying the electronic environment of the active element.

Suitably, the modification of the electronic environment is effected by the presence of at least one modifying moiety which is able to influence the electronic environment of the active element.

Suitably, the change in cycle time is due to transfer of energy to the modifying moiety from the lower level of the emission transition or another energy level having a lesser energy than the lower level of the emission.

Suitably, the cycle time is modified by changes in the conformation of the active element relative to a modifying moiety.

Suitably, each active element comprises part of a probe, whereby the probe is moved between different dielectric environments, including those occurring in a molecule or its solvent, wherein the characteristic cycle time of the probe is affected by the time scales of the motion of the active element between different dielectric environments, the motion being affected by modifications including at least one of the following:—
  (a) Altering the overall size of the probe:
  (b) Altering the distance between the active element and the remainder of the probe;
  (c) Altering the rigidity of a spacer molecule between the active element and the remainder of the probe; or
  (d) Modification of the probe or part thereof with hydrophilic, polar, charged or hydrophobic moieties.

Suitably, the active element comprises part of a species which periodically interacts with a modifying moiety, and the periods during which the species interacts with the modifying moiety and the periods during which the species does not interact with the modifying moiety are measured.

Suitably, the active element comprises part of a species which periodically interacts with a quenching moiety and is thereby quenched by a static quenching mechanism, and the periods during which the species is active and the periods during which the species is inactive are measured.

Suitably, the active element comprises part of a species which periodically interacts with a quenching moiety and is thereby quenched by a collisional quenching mechanism, and the periods during which the species is active and the periods during which the species is inactive are measured.

Suitably, the period of the periodical interaction is influenced by a suitable modification of a property of the species or the modifying moiety or quenching moiety.

Suitably, the modification comprises changing the length of a spacer molecule upon which the active element is located, or the length of the spacer molecule upon which the modifying moiety or quenching moiety is located.

Suitably, the modification comprises changing the flexibility of a spacer molecule upon which the active element is located, or the flexibility of the spacer molecule upon which the modifying moiety or quenching moiety is located.

Suitably, the modification comprises adding a modifying moiety to a spacer molecule upon which the active element is located, or to a spacer molecule upon which the modifying moiety or quenching moiety is located.

Suitably, the active element is attached via a spacer molecule to a binding site, and the modification results from an interaction with the binding site.

Suitably, the modification results from a restriction of periodic movement of the spacer molecule upon which the active element is located, or the spacer molecule upon which the modifying moiety or quenching moiety is located.

Suitably, the active element is attached via a spacer molecule to a binding site, and the modification results from an interaction with a modifying moiety attached to the binding site.

Suitably, the active element is attached via a first spacer molecule to a first binding site, and a modifying moiety or quenching moiety is attached via a second spacer molecule to a second binding site, wherein the separation of the first and second binding sites determines the periodicity of the interaction between the active element and the modifying moiety or quenching moiety.

The binding may be to split DNA/RNA probes, to complimentary DNA/RNA. The invention may be used to monitor binding of a ligand (for example a drug, hormone, etc) to a protein (for example an antibody, receptor, or synthetic mimic) either directly or indirectly (competitively).

Suitably, first and second elements periodically interact to form the active element, and the period during which the first and second elements interact to form the active element and the periods during which the first and second elements do not interact to form the active element are measured.

Any of the above described modifications of the interaction between an active element and a modifying moiety or quenching moiety may be applied to the periodic formation of an active element via interaction of the first and second elements. This may be done by replacing the active element with the first element, and replacing the modifying moiety or quenching moiety with the second element.

The active element formed by the first and second elements may be a fluorescence resonant energy transfer species.

The active element formed by the first and second elements may be an excimer or an exciplex.

Suitably, the excitation cross section of a ground state of an active element is varied periodically, and the period of variation is measured.

Suitably, the active element emits fluorescence photons which interact with a solution in which the active elements are held, and the effect of the solution is monitored by modulating properties of the solution.

Suitably, the method further comprises exciting the active elements using an excitation pulse and determining the time elapsed between excitation and the emission of a quanta from the active element, and then subtracting that time from the characteristic cycle time.

Any of the above modifications may be used to produce an active species with a characteristic cycle time to be used as a label, for example a DNA probe or ligand binding assay using antibodies or receptors.

The invention may be used to monitor conformational changes (for example of a protein) as the distance/juxtaposition changes. The invention may be used to identify residues assembled in a polymer (for example, combinatorial synthesis of peptides or oligonucleotides or oligosaccharides).

Fluctuations in the photon output which result from periodic absorption processes and associated relaxations caused by phonons via mechanical fluctuations may be measured according to the invention.

Excitation of the sample may be by other forms of energy (for example X ray fluorescence). Excitation of the sample may be via a chemical reaction (for example chemi-luminescence) or may involve other forms of energy (for example phosphorescence). The chemical excitation may include a catalyst, which may be an enzyme (for example, ATP and NADH driven bioluminescence).

The invention may be used to assay for a particular bacteria, virus, chemical, family or subgroup. The invention may be used for screening for chemicals, novel drugs, agricultural chemicals, food contamination, DNA, RNA, bacteria, viruses, or by-products indicating the presence or activity of these entities. The screening may be carried out serially or in parallel.

The active elements may have an upper excited state, a lower excited state and a ground state, and emit a detectable quanta upon relaxation from the upper excited state to the lower excited state, the method further comprising exciting second elements to an excited state such that the second elements transfer excitation energy to the active elements, thereby exciting the active elements to the upper excited state. The use of the second element is advantageous because the second element acts as a buffer, storing excitation, and passing the excitation on to the active element at a later time. This is particularly advantageous when the sample is excited by pulsed excitation or by excitation which fluctuates in intensity. The buffer will smooth ripples from an excitation signal in a manner analogous to a capacitor smoothing ripples from an electrical signal.

Suitably, many second elements are provided for each active element.

The detection of a quanta may be correlated with the detection of another property of the sample.

The quanta may be photons. The active elements may be fluorophores. The sample may comprise less than 100 active elements. The sample may comprise less than 10 active elements.

The characteristic cycle time may be in the range of 10–1000 ns. The method may be used to probe for biological materials, assaying materials or for multi-probing biological materials. The natural fluorescence of a sample may be used.

According to a second aspect of the invention there is provided an analysis apparatus for determining the characteristic cycle time of active elements in a sample, comprising means for exciting active elements in the sample with sufficient intensity that at least some of the active elements are re-excited to an excited state substantially immediately following relaxation to a ground state, means for detecting quanta emitted by the sample to obtain a detected signal, analysing means for analysing the detected signal to derive the characteristic cycle time, wherein the number of active elements in the sample and the intensity of the excitation are such that quanta are detected in a stream in which individual quanta are distinguishable from each other.

BRIEF DESCRIPTION OF THE DRAWINGS

Specific embodiments of the invention will now be described by way of example, with reference to the accompanying drawings, in which.

DETAILED DESCRIPTION OF EXEMPLARY EMBODIMENTS

Figure 1:
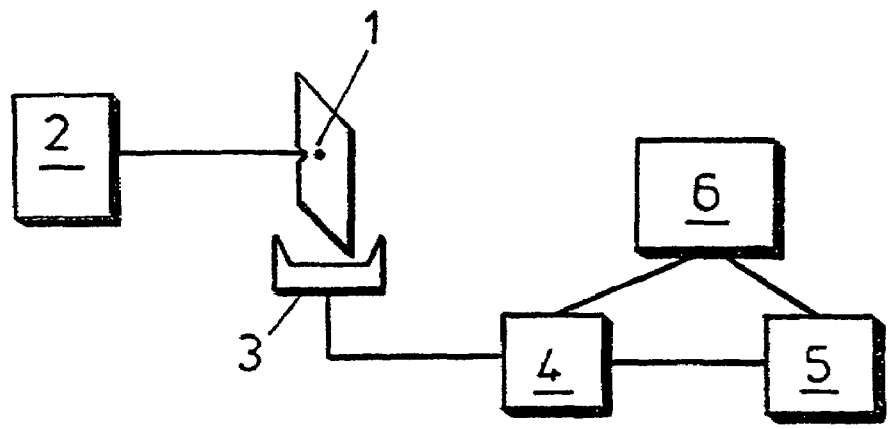
FIG. 1 is a schematic representation of a fluorescence detection apparatus according to the invention.

Referring first to FIG. 1, a fluorescence detection apparatus comprises a sample 1 and a laser 2 which is arranged to illuminate the sample 1 with a continuous beam of light. A detector 3 is provided to detect photons emitted by the sample 1. The detector 3 may be provided with a filter (not shown) to prevent the detection of light emitted by the laser 2. An auto-correlator 4 correlates the detected signal to give a correlation, and a processor 5 processes the output of the detector to measure the characteristic lifetime of the fluorophores comprising the sample 1. The operation of the processor 5 is described below. The output from the processor 5 and/or the auto-correlator 4 may be displayed on a monitor 6.

Figure 2:
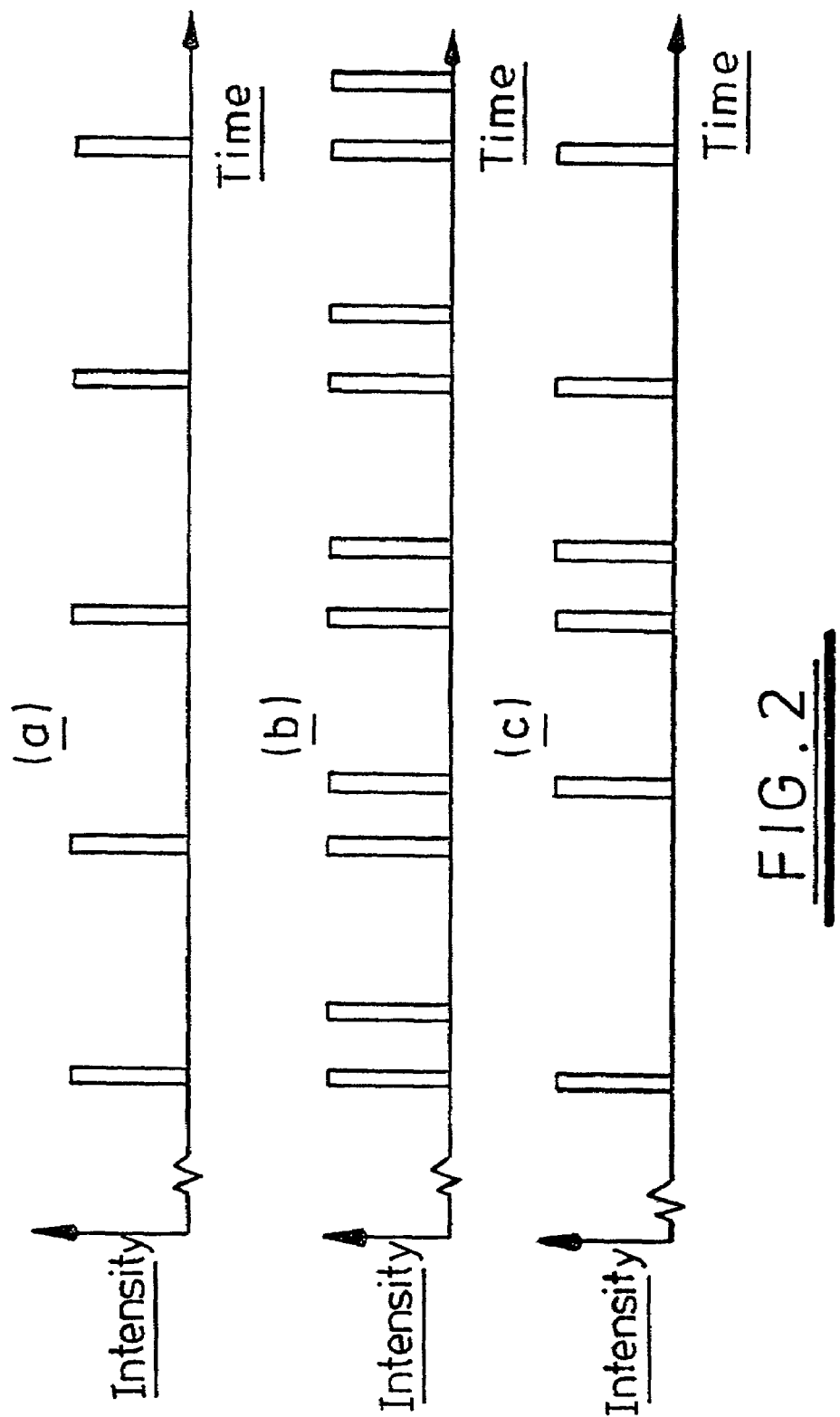
FIG. 2 is a set of graphs which illustrate the operation of the invention for a very small number of fluorophores.

FIG. 2 illustrates the principle of operation of the invention. FIG. 2a represents the result of illuminating a single fluorophore with a continuous beam of high intensity light. A photon in the high intensity beam will excite the fluorophore to an excited state, and following a time period characteristic of the fluorophore, the fluorophore will emit a photon (i.e. it will fluoresce). Upon emission of the photon the fluorophore will relax to a less energetic state, and will subsequently relax to a ground state. Since the fluorophore is being illuminated by a continuous stream of photons from the laser, once it has returned to its ground state it will be excited again immediately to its excited state. The fluorophore will again emit a photon following a characteristic time period. Thus, a series of photons will be emitted by the fluorophore, each photon being separated from the previous photon by the same period of time, as a illustrated in FIG. 2a. The separation of the photons corresponds to the time taken for a fluorophore to return to the ground state following excitation from the ground state. This period will be referred to as the characteristic cycle time of the fluorophore.

In FIG. 2a, signals corresponding to each photon emission are shown as being equally spaced. In fact, the characteristic cycle time will not be constant but will vary about a mean. Such variations are taken account of however by the auto-correlation process described above. Thus for the purposes of illustration only FIGS. 2a to 2c have been prepared on the assumption that the characteristic cycle time of the fluorophore is constant.

The graph shown in FIG. 2a illustrates an ideal scenario in which the sample comprises a single fluorophore, that every photon emitted by the fluorophore is detected, that the fluorophore is excited immediately when it decays to its unexcited state, that the fluorophore cannot be further excited when it is in the excited state, and that no light from the laser 2 is detected.

FIG. 2b illustrates a second scenario, where the sample comprises two fluorophores of a single type, and all of the other assumptions given above still apply. In this case, each fluorophore will emit a series of photons as above. The characteristic cycle time of the fluorophore is apparent from the separation of the photons in each series, as an auto-correlation of the photon distribution will provide a strong peak at a frequency which corresponds to the characteristic cycle time of the fluorophore.

FIG. 2c illustrates a third case which corresponds to that shown in FIG. 2b, except that not all of the photons emitted by the fluorophore are detected. Although not all of the emitted photons are detected, the number detected is sufficient that, an auto-correlation of the signal of FIG. 2c will yield a peak at the frequency which corresponds to the characteristic cycle time of the fluorophore, and there will now be a further peak at two times that frequency, a peak at three times that frequency, and so on.

Thus, it is not necessary that every photon emitted by a sample of fluorophores is detected, but rather all that is required is that the number of photons detected is sufficient for an auto-correlation of the detected signal to yield measurable peaks at multiples of the frequency which corresponds to the characteristic cycle time of the fluorophores.

There is an upper limit to the number of fluorophores which may be included in a sample. If for example a sample comprised more than 100 fluorophores, and the detector detected all photons emitted by the fluorophores, then the number of photons would be so great that the detected signal could become 'washed out' and it would difficult to obtain any information from the signal.

As stated above, in an ideal scenario a single fluorophore only would be measured. However, in practice the assumptions made for that ideal scenario will not hold. For example, not all of the photons emitted by the fluorophore will be detected. Furthermore, not all of the fluorophores included in a sample will be active. To maximise the signal-to-noise ratio of the detected signal, an optimum combination of sample size and intensity of laser illumination may be selected. The selection will depend upon the specific optical arrangement used, and will be influenced by, for example, the efficiency of detection of photons and the quantum efficiency of the fluorophore sample. Thus, the number of fluorophores to be used is determined experimentally by maximising the signal-to-noise ratio of the detected signal for given experimental conditions. The ideal signal level will correspond essentially to the observation of a single fluorophore in the ideal scenario as described above, although this will actually involve detecting a percentage of the emission of between approximately 5–50 fluorophores.

Figure 3:
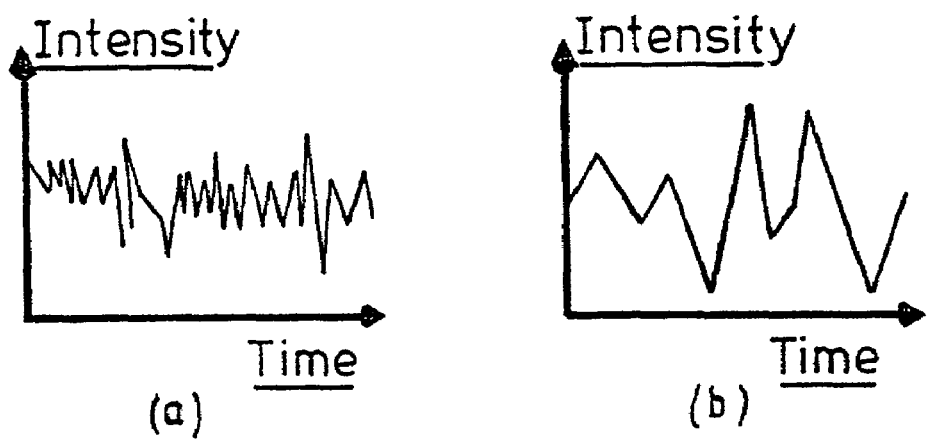
FIG. 3 is a set of graphs which illustrate the operation of the invention for a larger number of fluorophores.

FIG. 3 illustrates the operation of the invention close to its upper limit (in terms of intensity of detected light). If apparatus as shown in FIG. 1 is used to detect photons emitted by a sample of a large number of fluorophores, for example 50, a detected signal as shown in FIG. 3a may be obtained. Rather than detecting individual photons separated by time delays, the number of fluorophores is such that the intensity of detected fluorescent light never falls to zero. Although the detected signal appears to be random, from the above it will be understood that an auto-correlation of the signal will yield a series of peaks which are multiples of a frequency which corresponds to the characteristic cycle time of the fluorophore, thus allowing the fluorophore to be characterised. This is further illustrated with reference to FIG. 3b, where again the detected signal appears to be random. Assuming that the sample from which the symbols of FIGS. 3a and 3b are derived include the same number of fluorophores, the signal shown in FIG. 3b corresponds to a fluorophore with a characteristic cycle time which is ten times that of the characteristic cycle time shown in the signal of FIG. 3a. Although both FIGS. 3a and 3b appear to have random signals, it is apparent from the number of times that the signal crosses its mean value that the characteristic cycle time of the sample detected in FIG. 3b is less than that of the sample detected in FIG. 3a.

The above described embodiment assumes that the intensity of light incident on a sample is sufficient such that once a given fluorophore has returned to its ground state it will immediately be excited to an excited state. This is the optimum experimental set-up since a signal detected under these conditions will be a function only of the characteristic cycle time of the fluorophore. If a lesser intensity of incident light were used, then the separation of the photons emitted from a given fluorophore would be a function of the characteristic cycle time of the fluorophore and the time elapsed between photons colliding with the fluorophore. The rate of photon collision will be constant for a given laser intensity and experimental set-up, and the effect of a less than optimum intensity of incident light may be removed from the measured cycle time via suitable calibration in order to obtain the characteristic cycle time.

The laser shown in FIG. 1 is described as being arranged to illuminate a sample with a continuous beam of light. This is an advantageous arrangement, since continuous wave (CW) lasers are cheap and widely available. However, it will be understood that the sample may be illuminated using pulsed light. For example light having an interpulse separation of the order of or less than the characteristic cycle time of the sample fluorophores. If the interpulse separation were to be greater than this then the amount of time spent by each fluorophore in an unexcited state would introduce noise into the detected signal to such an extent that fluorophore lifetime measurement would be compromised.

A sample of fluorophores may be illuminated with pulses having a duration much longer than the characteristic cycle time of the fluorophores comprising that sample. For example, a pulse of 10 microseconds produced by a Q-switched laser may be used to measure fluorophore characteristic cycle times of the order of 1 nanosecond. This is possible because the pulse is 10,000 times longer than the cycle time, and sufficient photons will therefore be emitted during a given excitation pulse for a measurement of the characteristic cycle time to be obtained.

If the duration of an excitation pulse is equal to $(100 \times \tau)^2$ where $\tau$ is the characteristic cycle time of a fluorophore to be measured this will allow a maximum possible signal to noise of the order of one percent. The pulse duration must be at least an order of magnitude greater than the characteristic cycle time to be measured, in order to provide a useful measurement.

The measurement of a characteristic fluorophore cycle time using a single pulse contrasts with conventional fluorescence analysis, where many thousands of illumination pulses are needed to measure a characteristic fluorophore lifetime.

The characteristic cycle time of a fluorophore may be derived from the detected signal in several ways, including using signal analysers, analogue correlators, storage and software correlation or Fourier transforms.

The invention may be used to study the quantum efficiency of fluorophores. Quantum efficiency is a measure of the number of photons emitted by a fluorophore in relation to the number of photons 'absorbed' by that fluorophore.

Generally, a photon will, upon absorption by a fluorophore, excite that fluorophore to a state from which it will relax to a lower state by the emission of a photon (this is fluorescence). However, some excited states of a fluorophore will not allow the emission of a photon, and the excitation must be dissipated in some other way, for example as heat. A 'non-fluorescent' excited state may or may not be capable of being excited further to a 'fluorescent' excited state by absorption of a further photon. Known prior art fluorescence detection apparatus requires a sample of many fluorophores, and it is not possible to perform a full study of the quantum efficiency of a given type of fluorophore, since the effect of excitation to 'non-fluorescent' states is averaged out for all fluorophores in the sample. The invention allows the study of a sample comprising a very small number of fluorophores, which thereby allows more detailed investigation of 'non-fluorescent' states.

Figure 4:
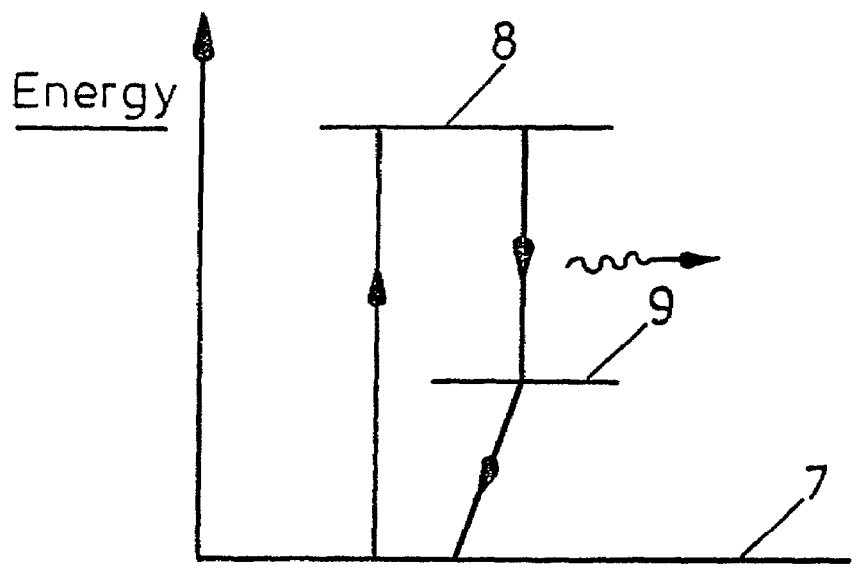
FIG. 4 is a schematic illustration of the energy states of a fluorophore.

FIG. 4 shows schematically the energy states of a simple fluorophore. The fluorophore begins at a ground state 7, is excited to an upper level of an emission transition 8 by energy from an outside source and decays from the upper level of the emission transition 8 to a lower level of the emission transition 9, and simultaneously emits a photon. The fluorophore then decays from the lower level of the emission transition 9 back to the ground state 7.

In a conventional measurement of fluorescence lifetime an incident laser pulse is used to excite a fluorophore (within a population) from the ground state 7 to the upper level of the emission transition 8, and a measurement is made of the time elapsed until a photon is emitted from the fluorophore. The time period measured is the time from excitation from the round state 7 until the emission transition takes place. The present invention allows the detection of a series of photons emitted from a fluorophore which is continually excited so that it spends effectively no time at the ground state 7. The characteristic cycle time measured using the invention is the sum of the lifetimes of the upper level of the emission transition 8 and the lower level of the emission transition 9. Since the lifetime of the lower level of the emission transition 9 is not included in the period measured using conventional fluorescence detection, the lifetime of this lower level 9 may be determined by subtracting the lifetime measured using the conventional fluorescence detection from the characteristic cycle time measured using the invention.

The lifetime of the lower level of the emission transition 9 could be measured for example using a laser which is configured to produce pulsed radiation to allow a conventional fluorescence measurement, and then configured to produce continuous light so that the characteristic cycle time the fluorophore may be measured using the method according to the invention. Detection apparatus may be configured to automatically subtract the conventionally measured characteristic fluorophore lifetime from the characteristic cycle time, to provide a measurement of the lifetime of the lower level of the emission transition 9. In some cases the conventionally measured fluorescent lifetime of a fluorophore may already be known, in which case the lifetime of the lower level of the emission transition 9 may be determined by subtracting the known lifetime from the cycle time.

It is advantageous to maintain the fluorophore of FIG. 4 in a substantially continuous excitation cycle. The effect of a less than optimum rate of excitation of the fluorophore from the ground state will be included in the measured characteristic cycle time, and will reduce the accuracy of the cycle time measurement. This effect may be reduced using experimental calibration.

Figure 5:
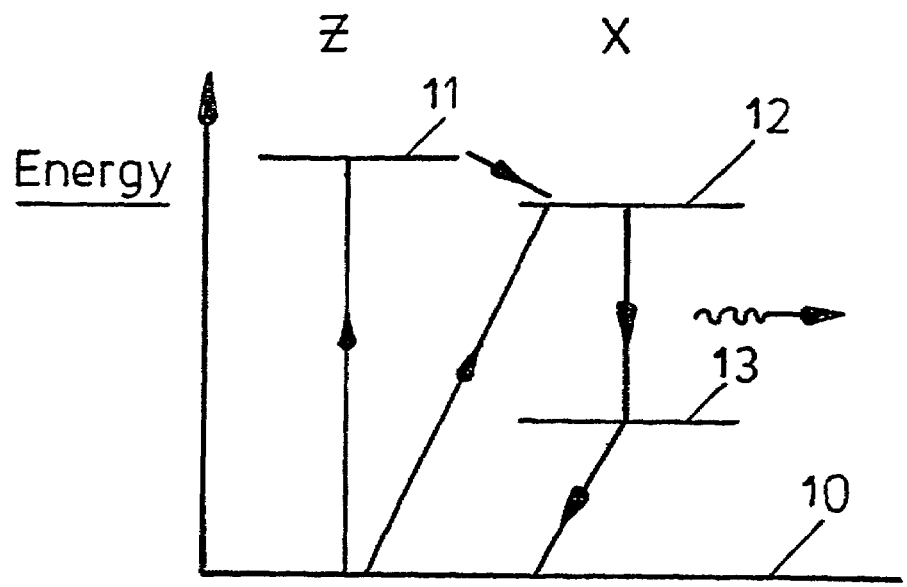
FIG. 5 is a schematic illustration of the energy states of a fluorophore and the energy states of a molecule.

FIG. 5 illustrates an advantageous way of providing the required continuous excitation. A sample containing fluorophore X is provided with molecule Z. Molecule Z is excited by incident illumination from a ground state 10 to an excited level 11. Fluorophore X is excited to an upper level of an emission transition 12 by collision with molecule Z, relaxes via a radiative emission to a lower level of the emission transition 13, and then relaxes to the ground state 10 (the ground state 10 is common to both X and Z). The excited level 11 of molecule Z has a longer lifetime than the upper level of the emission transition 12 of fluorophore X. Molecule Z thus acts as a buffer, storing energy in the excited level 11, before transferring the energy to fluorophore X. The use of molecule Z is analogous to a capacitor in an electric circuit which stores electrical energy and releases it into the circuit over time. Fluorophore X may occasionally be excited directly to the upper level of the emission transition 12 by the illumination, as shown in FIG. 5.

Very many molecules Z should be provided for each fluorophore X, to ensure that there are plenty of excited molecules Z to interact with and excite the fluorophore X to the upper level of the emission transition 12 when it has decayed to the ground state 10. The molecule Z must have an excited level 11 lifetime greater than the interpulse separation time if this arrangement is to be used to avoid ripple caused by pulsed illumination.

Where many molecules Z are provided for each fluorophore X, the majority of the illumination will excite molecules Z rather than directly exciting fluorophores X. If the fluorophores X were excited directly by illumination then there would be a significant probability of two excitation photons being absorbed by a given fluorophore X within a short time, such that that fluorophore would be excited to a very high energy level. In contrast to this, the molecules Z are provided with a finite amount of energy by the illumination, and thus cannot excite the fluorophores X to very high states. The use of molecules Z as illustrated in FIG. 5 thus reduces the probability of a fluorophore X being over excited and becoming quenched.

An example of the excitation of a fluorophore X via a molecule Z is Fluorescence Resonant Energy Transfer (FRET), wherein a first fluorophore transfers energy via a dipole—dipole interaction to a second fluorophore. The FRET mechanism is described in detail below. In order for the FRET mechanism to act as a buffer, many donor molecules (the first fluorophore) are required for each acceptor molecule (the second fluorophore). A lysine tree may be constructed, beginning with an acceptor and placing donors on the rest of the tree.

Where a fluorophore has a significant energy state (or states) below the lower level of an emission transition, or above the upper level of an emission transition, considerable localised heating may be generated during decay from those energy levels. The localised heating may generate a number of low energy phonons, which may appear as an analogue signal. The effect of this heating may be measured in several ways, for example by direct temperature measurement, local pressure difference measurement, and refractive index change. The method according to the invention may be modified so that an event will only be registered if a photon is detected and the state of localised heating is above a predetermined state. Alternatively, the detected photon arrival stream and the localised temperature may be cross-correlated (in order to do this the localised temperature must be represented by a digital number). The combination of an analogue signal with a signal detected according to the invention may be used in any other suitable application. Furthermore, it will be understood that fluctuations in the photon output which result from periodic absorption processes and associated relaxations caused by phonons via mechanical fluctuations may be measured according to the invention.

The photons emitted by a sample of fluorophores which is excited according to the invention may be considered to some extent to be coherent. This coherent fluorescent light may be mixed with coherent light from a second source (for example the excitation source, which may be a laser) to provide a beat signal. The beat signal is useful because it will have a frequency lower than the frequency which corresponds to the cycle time of the fluorophores comprising the sample. If a portion of the excitation signal is directed at a detector along with the emission signal, beats will be seen at the detector, the beats having a frequency corresponding to the difference between the frequencies of the excitation pulses and the characteristic cycle time.

In an alternative arrangement the first and second sources of coherent light may be first and second types of fluorophores in a single sample. The use of beat frequencies is ideally suited to detecting small changes in the characteristic cycle time of a fluorophore. For example, a sample may comprise a single type of fluorophore with a single characteristic cycle time of 100 ns. If the properties of half of that sample are modified slightly so as to change slightly the characteristic cycle time of that half of the sample to 95 ns, then a beat frequency of 500 kHz indicative of the cycle time change will be detected.

The invention allows the measurement of characteristic cycle times of chemiluminescence species (i.e. species which are excited chemically, and emit photons during relaxation to a lower state). In this case, the measured lifetime is a roll-over of a catalyst (which may be an enzyme), rather than a decay of a fluorophore. Where sufficient quantities of catalyst or enzyme are provided, a chemi-luminescent species may spend substantially zero or comparatively little time at a ground state, but will cycle continuously to an upper level of an emission transition and emit photons separated by a period corresponding to the time taken for the species to be excited from a ground state to upper level of the emission transition and relax back to the ground state. Similarly, the invention also allows the measurement of lifetimes of bio-luminescent species.

Lifetimes of chemi-luminescent and bio-luminescent species cannot be measured easily using conventional fluorescence lifetime measurement techniques. This is because the conventional techniques require excitation of a species to occur at a known time, so that the time until photon emission following that excitation may be measured. Excitation of chemi-luminescent and bio-luminescent samples at a specific predetermined time cannot easily be provided.

An example of an enzyme triggered chemi-luminescence assay is the assay for adenosine triphosphate (ATP), which indicates the presence of viable bacteria. Luciferase enzyme is added to a sample under test along with the substrate luciferin. In the presence of ATP the luciferin is activated, and the activated luciferin produces a luminescent output in the presence of oxygen:

Luciferin+ATP+$O_2$⇒ (in the presence of luciferase+ $Mg^{++}$) ⇒oxyluciferin+AMP+Ppi+$CO_2$+photon (560 nm)

The method according to the invention will measure a time signature dependant on the average delay between ATP/luciferin contact, the average delay between $O_2$/luciferin contact, the time required for luciferase catalysis turnover (effectively an enzyme lifetime), and the upper state lifetime of luciferin in the presence of oxygen. The time scale of the two contact delays may be modified by the quantity of each chemical present. This is in contrast to the turnover time and the upper state lifetime which are characteristic lifetimes and are therefore independent of the quantities of each chemical present.

In the case of chemi-luminescence the characteristic cycle time measured using the continuous detection method as described above may include a chemical reaction due to a chemical interacting with a catalyst, changing to a new form and emitting a photon, and then moving away from the catalyst allowing it to begin a new interaction.

The invention may be used to make stopped-flow fluorescence measurements. Stopped-flow measurements are used to measure interactions between a fluorescent probe and a sample which take place on a rapid time scale. A fluorescent probe is excited continuously, avoiding the need to synchronise the excitation with the mixing of the probe and sample. The method is advantageous because it avoids synchronisation problems, and has the further advantage that the period of time over which the interaction may be monitored is unlimited.

Referring to FIG. 4, the characteristic cycle time of a fluorophore may be modified by altering the lifetime of the upper level of the emission transition 8 or the lifetime of the lower level of the emission transition 9.

Figure 6:
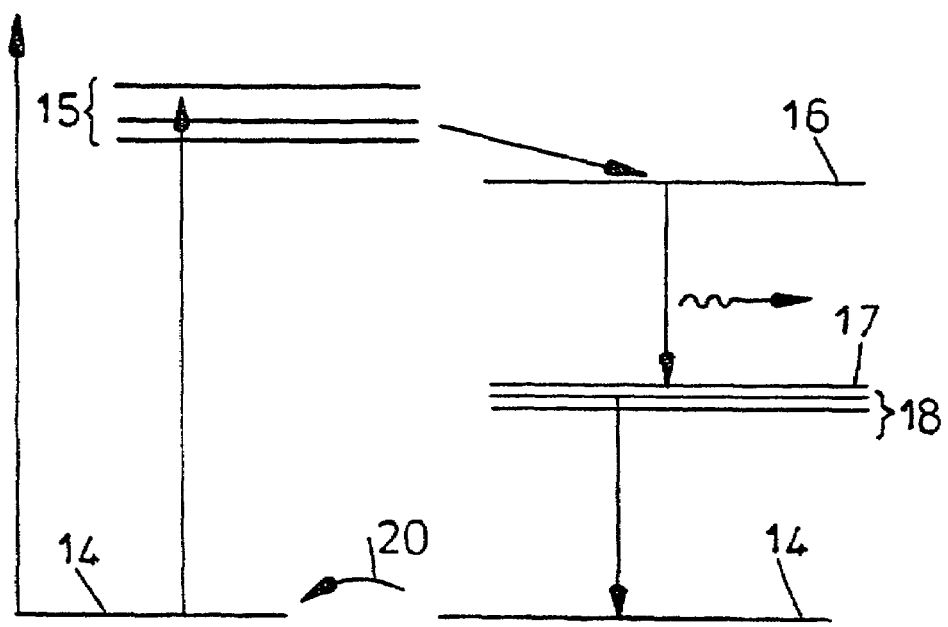
FIG. 6 is a schematic illustration of the energy states of an active species.

FIG. 6 is a schematic illustration of an active species which is more complicated than the simple fluorophore illustrated in FIG. 4. The active species shown in FIG. 6 includes a ground state 14, and a group of excited levels 15. The excited levels 15 comprise an excited state which is broadened into a group of closely spaced levels by an effect such as vibrational broadening. Once the active species has been excited to one of the excited levels 15, it may relax to a less energetic one of the excited levels 15.

The active species will decay from the group of excited levels 15 to an upper level of an emission transmission 16. The active species will then decay via a radiative emission to a lower level of the emission transmission 17. Further levels 18 having an energy slightly less than the lower level of the emission transmission 17 are termed post emission levels 18. The active species may relax to one or more of these post emission levels 18, before decaying to a ground level 19.

The ground level 19 is shown as being distinct from the ground state 14 in order to represent, for example, a conformational change of the active species. The active species may be such that it must be in a specific conformational arrangement before it can be excited to the excited levels 15. Upon relaxation from the post-emission levels 18 to the ground level 19, the active species is not in the required conformational arrangement, and thus cannot be excited. Following a conformational change of the active species, represented by the arrow 20 connecting the ground level 19 to the ground state 14, the active species may then be excited.

The terms ground level 19 and ground state 14 are used to distinguish between the conformational arrangements. Conformational changes of the active species may occur if the active species comprises two parts. Other changes may include periodic changes of the probability of an excitation from the ground state 14 occurring, for example due to cyclic movement of a fluorophore towards and away from a quenching moiety (the fluorophore and the quenching moiety together comprising the active species). This is effectively a periodic variation of the excitation cross-section of the active species, and is not represented in FIG. 6.

Each of the levels 14–19 shown in FIG. 6 has a lifetime. Some of the lifetimes may be much longer than others, depending upon the nature of the active species. The characteristic cycle time of the active species is the time elapsed between excitation of the active species from the ground state 14 until the next excitation of the active species from the ground state 14.

The characteristic cycle time may be modified by altering the lifetime of any of the levels mentioned above. This is in contrast to the conventionally measured characteristic lifetime of an active species, which includes only the lifetimes of the excited levels 15 and the upper level of the emission transition 16. The measurement of the characteristic cycle time thus provides much greater flexibility with regard to modifying time characteristics of an active species. The modifications will in general result in an increase of the characteristic cycle time of the active species.

The lifetime of the lower level of the emission transition 17, and the lifetimes of the post-emission levels 18 may be modified in a number of ways. These include changes of the local environment, for changes of temperature, pH, pressure, the ionic strength of a solution containing the active species, or the application of a magnetic or electric field. The lifetimes may also be shifted by changes of the conformation of the active species. Many methods of modifying the lifetimes of the excited levels 15 and the upper level of the emission transition 16 are known in the prior art. These methods may also be used to modify the lifetime of the lower level of the emission transition 17, and the lifetimes of the post-emission levels 18.

The lifetime of the post-emission levels 18 may be a combination of many lifetimes, for example dissipation by electromagnetic radiation, vibration, rotation or by a quenched lifetime or transition via another element.

During measurement of the characteristic cycle time of an active species, there may be a delay between the relaxation of the active species to the ground state 14 and subsequent excitation from the ground state 14. This delay may be due to the intensity of excitation being less than optimum. The delay will nevertheless be recorded as part of the characteristic cycle time of that active species. The effect of this delay may be removed from the characteristic cycle time measurement by experimental calibration. The delay may be due to for example a periodic variation of the excitation cross-section of the ground state 14. Again, this delay is included in the characteristic cycle time measurement. This delay will not be removed by experimental calibration since it is property of the active species.

As mentioned above, in order for a meaningful measurement of the characteristic cycle time to be obtained, the elapsed time during which an active species is at the ground state 14 must be less than the sum of the lifetimes of the other levels 15–18 (or 15–19 if the active species includes a ground level 19 as described above). If the excitation cross-section of the ground state 14 is affected by the presence of a substance of interest, then the lifetime of the ground state 14 will be modified when that substance is present. This will provide a change of the characteristic cycle time, which may be detected. The lifetime of the ground state may therefore be used as a marker assay. In general, any effect which modifies the lifetime of the ground state 14 may be monitored using the method according to the invention, provided that the lifetime of the ground state 14 both before and after modification is less than or equal to the sum of the lifetimes of the other levels 15–18 (or 15–19).

An active species may comprise a simple fluorophore. Alternatively, the active species may comprise a combination of elements, for example a fluorophore, a quenching moiety, and a further element linking them together. In other words, a fluorophore is the part of the active species which generates a photon, but the ensemble of moieties (chemicals, particles, etc.) which together produce a characteristic cycle time of interest is termed the active species. The characteristic cycle time of the 'active species' may differ from that of a corresponding simple fluorophore. The characteristic cycle time may be influenced for example by a quenching moiety.

A quenching moiety may be arranged to provide quenching in several different ways. For example, in a so called 'static quenching' arrangement a fluorophore and a quenching moiety may combine to form an inactive complex (molecule), which cannot be excited so as to emit a photon. Referring to FIG. 6, the inactive complex remains at the ground level 19 and cannot be excited. When the complex breaks down, the fluorophore may then be excited. The periodicity of the complexation/decomplexation process may be measured according to the invention, as described below.

A quenching moiety may be held in proximity to a fluorophore such that it periodically approaches and recedes from the fluorophore. The probability of the quenching moiety and the fluorophore combining to form an inactive complex will vary periodically with this motion. The time elapsed before the inactive complex is formed will be characteristic of the configuration of the fluorophore and the quenching moiety. Following formation of the inactive complex, the inactive complex will separate back into its constituents, namely the fluorophore and quenching moiety, after a further characteristic time.

The invention may be used to measure the periods during which the fluorophore is active, and the periods during which the fluorophore is inactive due to the effect of the quenching moiety. Since the fluorophore is excited continuously, it will emit a series of fluorescence photons separated by the characteristic cycle time of the fluorophore. The fluorophore will continue to emit photons until it forms an inactive complex with the quenching moiety. No further photons will be emitted until the inactive complex separates back into its constituents. A correlation, or other suitable transformation of the detected photons will yield components indicative of the period during which photons were emitted and the periods during which no photons were emitted.

When considering a single fluorophore, it is apparent that it would not be possible to measure the periods during which the fluorophore was active, or the periods during which the fluorophore was inactive using conventional fluorescence lifetime measurement. This is because successive excitation pulses used in conventional measurement are widely spaced in time. The conventional measurement is only capable of measuring a single quantity, that is the time elapsed between excitation from the ground state of a fluorophore until emission of a fluorescence photon.

One arrangement via which static quenching may be achieved is illustrated schematically in FIG. 7a. A fluorophore 21a is attached by a flexible spacer molecule 22a to a binding moiety 23a (these elements taken together may be described as a probe). The binding moiety 23a is configured to bond to a predetermined binding site 24a in a predetermined molecule. The curved line located above the fluorophore 21a is representative of the periodic motion of the fluorophore 21a via flexing of the spacer molecule 22a.

A quencher moiety 25a is attached to the binding site 24a. The probability of the fluorophore 21a and the quenching moiety 25a combining to form an inactive complex increases as the fluorophore 21a approaches the quenching moiety 25a. When an inactive complex is formed (not shown) it will remain in existence for a characteristic time, following which the fluorophore 21a will no longer be influenced by the quenching moiety 25a and will again be free to move periodically via flexing of the spacer molecule 22a.

In a second known form of quenching, known as collision quenching, a fluorophore which has been excited to an upper level of an emission transition (i.e. level 16 in FIG. 6) collides with a quenching moiety. Upon collision with the quenching moiety energy is transferred from the fluorophore to the quenching moiety, and the fluorophore thereby relaxes to the ground state (level 14 in FIG. 6) without the emission of a photon. The fluorophore is prevented from being excited to an upper level of an emission transition (level 16 in FIG. 6) when the fluorophore is adjacent to the quenching moiety, since the fluorophore will be made immediately to relax to the ground state again by the quenching moiety. The quenching moiety may be a second form of fluorophore which is not active (energy being transferred by a dipole—dipole interaction).

It is important to distinguish between collision quenching (also known as dynamic quenching), whereby a fluorophore is returned to its ground state without emission of a photon, and static quenching, whereby a complex is formed by a fluorophore and a quenching moiety which prevents the fluorophore returning to its ground state.

The rate at which collision quenching occurs may be measured using the invention. Collision quenching may be arranged to occur with a configuration of fluorophore 21a and quenching moiety 25a as shown in FIG. 7a. The configuration is the same as that described above in relation to static quenching, the primary difference being that the quenching moiety 25a is chosen such that it will not form a molecule with the fluorophore 21a. The fluorophore 21a moves periodically as the spacer molecule 22a flexes, such that the fluorophore 21a approaches and recedes from the quencher moiety 25a. When the fluorophore 21a is sufficiently close to the quencher moiety 25a, energy is transferred from the fluorophore 21a to the quencher moiety 25a, and the fluorophore relaxes to the ground state without emission of a photon.

The rate of occurrence of collision quenching may be measured using the invention. For example, if the characteristic cycle time of the fluorophore 21a is short compared to the period of oscillation of the fluorophore 21a upon the flexible spacer molecule 22a, the fluorophore 21a may emit for example nine fluorescence photons before collision quenching occurs. Thus, the fluorophore 21a will emit a series of regularly spaced photons, every tenth photon being missing from the series. The photons are detected according to the invention and are transformed using a correlation or other suitable transformation. The transformed data will include a signature representative of the rate of occurrence of collision quenching.

The rate of occurrence of collision quenching may be measured using the invention, even where the efficiency of photon detection is not sufficient to detect every photon emitted by the fluorophore. This is because photons not detected due to experimental limitations will be random in distribution, whereas collision quenching will provide regularly spaced gaps in the series of photons, which gaps will provide a signature when the detection data is transformed.

The prior art method of measuring fluorescence lifetimes, when considering a single fluorophore is not capable of measuring the rate of occurrence of collision quenching. It provides no mechanism for actually measuring period over which the fluorophore is capable of emitting photons, or the period over which the fluorophore is quenched.

A further form of quenching is related to collision quenching. In this case, the fluorophore and quenching moiety do not actually collide (i.e. approach sufficiently for energy transfer to take place), but instead they simply approach sufficiently close that the quenching moiety has an effect on the energies and lifetimes of the levels of the fluorophore (14–18 in FIG. 6). Prior art methods of measuring fluorescence lifetimes are capable of measuring the effect of the quenching moiety on the lifetimes of the excited levels 15 and the upper level of the emission transition 16. The invention is advantageous because it measures the effect of the quenching moiety on the lifetimes of all of the levels of the fluorophore (14–18).

When considering FIG. 7a, it is apparent that if the spacer molecule 22a were to be rigid, then the effect of the quenching moiety 25a would be constant, and would not be dynamic (i.e. would not vary periodically). In this situation the characteristic lifetime of the fluorophore 21a as measured by prior art methods would appear as an exponential. However, if the spacer molecule were to be flexible (or longer) such that the interaction with the quenching moiety 25a was periodic, then the characteristic lifetime as measured by prior art methods would no longer be a simple exponential. As the interaction between the fluorophore 21a and the moiety 25a becomes more complex, the prior art methods become unable to make a meaningful measurement of the characteristic lifetime. In contrast to this, the invention provides a microscopic analysis, allowing individual relaxations of fluorophores to be seen.

A form of apparent quenching occurs when a medium in which fluorophores are held is sufficiently turbid or optically dense to reduce the observed fluorescent output from the fluorophores. If a modulation is applied to the real or imaginary part of the refractive index of the medium then the invention may be used to detect this modulation.

The fluorophore may interact with a modifying moiety that is not a quenching moiety. For example, energy may be transferred from a lower level of the emission transition (level 17 in FIG. 6) during a collision with a moiety. This will have the effect of returning the fluorophore to the ground state (level 14 in FIG. 6) more rapidly than would have been the case in the absence of the modifying moiety, thereby shortening the characteristic cycle time of the fluorophore.

The characteristic cycle time of the fluorophore will be affected by the dielectric environment in which it is located. For example, referring to FIGS. 7a–c, the extent to which the fluorophore 21a–c extends out of the binding site will affect its characteristic cycle time, as a result of the dielectric forces both inside and outside of the binding site. The spacer molecule 22a–c may contract and lengthen (typical vibrational motion) and this may cause a period variation of the characteristic cycle time of the fluorophore 21a–c.

Most fluorophores will self-quench when provided at high concentrations, for example fluorescein. A structure may be assembled to bring sufficient numbers of such fluorophores into close proximity such that self-quenching will occur. Self quenching may occur between proximal fluorophores, e.g. fluoroscein and calcein, or between different fluorophore molecules. The technique is most commonly applied in the use of Molecular Beacons, for example as described in S. Tvagi and F. R. Kramer, Nature Biotechnology, 1996, 14, 303, D. P. Bratu and F. R. Kramer, Nature Biotechnology, 1998, 16, 49 and L. G. Kostrikis et al, Science, 279, 1228. Usually the Molecular Beacon probe contains a fluorophore in proximity to a quencher, so that when the probe interacts with the target molecule the fluorophore and the quencher are separated and the fluorescence emission increases as a result.

The form of the structure assembled to bring sufficient numbers of such fluorophores into close proximity such that self-quenching will occur may be arranged to allow modulation of the self-quenching, which may be measured using the invention.

The use of quenching moieties is well known, and many quenching moieties are known in the art. Some gases are quenchers: notably molecular oxygen (of many fluorophores, for example perylene, ethidium bromide), but also xenon, nitrous oxide and nitromethane. These gaseous quenchers would not be normally assembled into fluorophore—quencher assemblies, but gas binding or intercalating structures (e.g. in the case of oxygen perfluorcarbons) can be used to modulate the level of oxygen in the vicinity of many fluorophores. In the case of free molecular gases, the collisional frequency between the fluorophore and gas molecules can be measured using the invention, whereas only an average shift in conventional lifetime is measurable as the dispersion of the population of decays.

Aromatic and aliphatic amines are effective quenchers of most unsubstituted fluorophores. For example, anthracene fluorescence is quenched in proximity to diethyaniline moiety, the quenching mechanism being a charge transfer during formation of a complex, the excited state fluorophore accepting an electron from the amine. In non-polar solvents, the complex formed may itself be fluorescent. Where a solvent is polar the emission of fluorescence photons from the complex is much less likely.

Other quenching moieties which provide collisional quenching include hydrogen peroxide and peroxide moieties (often resulting in bleaching effects as well), acrylamides, tryptophan, N-acetyl-L-tryptophanamide, bromates, iodides, nitroxides, olefins and sterically hindered saturated hydrocarbons. For example, alpha-cyanonaphthelene is quenched by a number of olefines, usually forming an non-fluorescent exciplex. Halogens (chloroform, trichlorethanol, bromobenzene, methyl mecuric chloride) act as collisional quenchers, and modifications bearing more than one chlorine atom usually act as quenchers. Quenching by large halogen modifications may be the result of intersystem crossing to an excited triplet state, promoted by spin-orbit coupling of an excited (singlet) fluorophore and halogen. As emission from the triplet state is slow, it is usually then quenched by many other process.

Indole, carbazole and their derivatives are sensitive to quenching by chlorinated hydrocarbons, and by electron scavengers (histidine, cysteine, fumarate, copper, lead, cadmium and manganous ion), involving donation of an electron from the fluorophore to the quencher. Indole, tryptophan and derivatives are quenched by succinimide, dicgloroacetamide, pyridinium hydrochloride, imidazolium hydrochloride, methionine, europium, silver and caesium ions.

Purines, pyrimidines, N-ethyl nicitonamide, N-alkyl pyridinium and picolinium salts are quenchers. For example, flavine and reduced nictonamide are quenched by adenine moieties, and 10-methylacridinium is quenched by guanosine-5-monophosphate.

Figure 7:
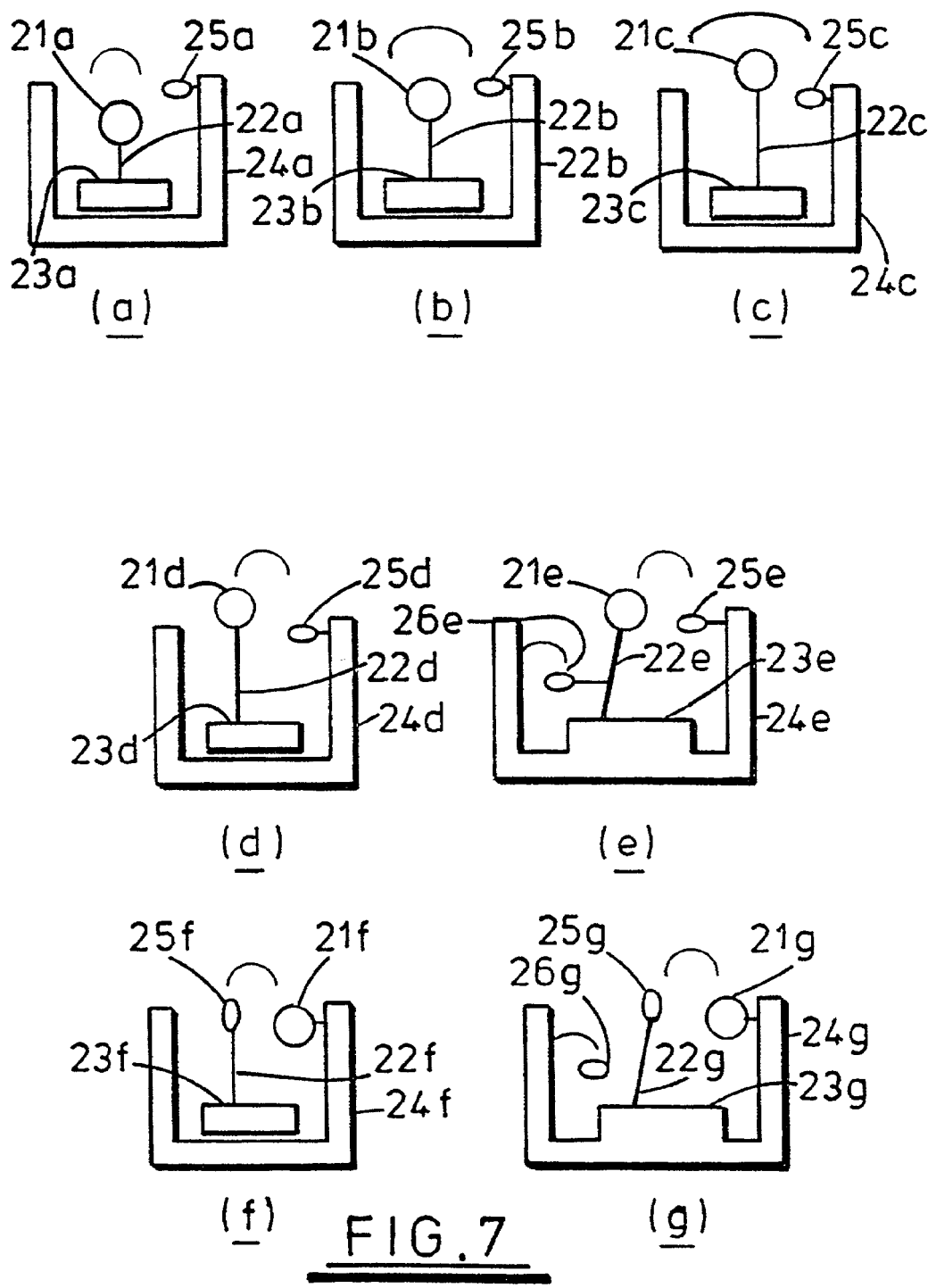
FIG. 7 is a schematic illustration of various configurations of active species, together with a graph illustrating quenching.

Referring to FIG. 7, various arrangements are shown by which the rate at which a fluorophore and quenching moiety approach each other may be modified. In each of FIGS. 7a–g a fluorophore is represented as a circular disk 21a–g and a quenching moiety is represented as an elliptical disk 25a–g, 26g. Flexible spacer molecules 22b–g, binding moieties 23b–g and binding sites 24b–g are represented in the same manner as in FIG. 7a.

FIGS. 7a–c represent the lengthening of the flexible spacer molecule 22a–c. As the spacer molecule is lengthened it will increase the time period between successive interactions of the fluorophore 21a–c and quenching moiety 25a–c.

The spacer molecule may also include a modifying moiety which further affects the dielectric environment of the binding site and consequently the characteristic cycle time of the fluorophore. FIGS. 7(d)–(e) show one possible effect of a modifying moiety 26e on the configuration of the fluorophore 21e within the binding site 24e. In this case the modifying moiety forces the fluorophore 21e closer to the quenching moiety 25e, thereby reducing the period between successive interactions of the fluorophore 21e and the quenching moiety 25e.

FIGS. 7(f)–(g) illustrate the case where a fluorophore 21f,g is attached directly to the binding site 24f,g and a probe molecule comprises a quenching moiety 25f,g attached by a flexible spacer molecule 22f,g and a binding moiety 23f,g to the binding site 24f,g. The period between successive interactions of the fluorophore 21f,g and the quenching moiety 25f,g is influenced, as before, by the length of the flexible spacer molecule 22f,g. A modifying moiety 26g may be attached to the flexible spacer molecule 22g.

The structures shown schematically in FIG. 7 may be constructed using the fluorophores and quenching moieties mentioned above. It is well known that many fluorophores are provided with chemically modifiable groups rendering their attachment to structural frameworks straightforward (an extensive list of commercially available fluorophores is described in the catalogue issued by Molecular Probes Inc., 4849 Pitchford Avenue, Oreg., 97402-9165 USA). Molecular modelling and Nuclear Magnetic Resonance (NMR) are well known techniques used to design such structures.

The system illustrated in FIG. 7 may be a drug binding to a protein or peptide comprising fluorescent amino acids at the site of binding. Such an example is given by the peptide sequence VCDWWGWGIC, known as a mimic of the binding of drugs by the drug efflux protein P-glycoprotein, which may be formed as a linear sequence or cyclised, whose natural tryptophan fluorescence is quenched by a range of drugs (Doxorubicin, Vinblastine, Genistein, Cyclosporin A, Erythromycin, Verapamil, Colchicine, Reserpine, Digoxin, Novobiocin, Diazepam, Melphalan).

Figure 7H:
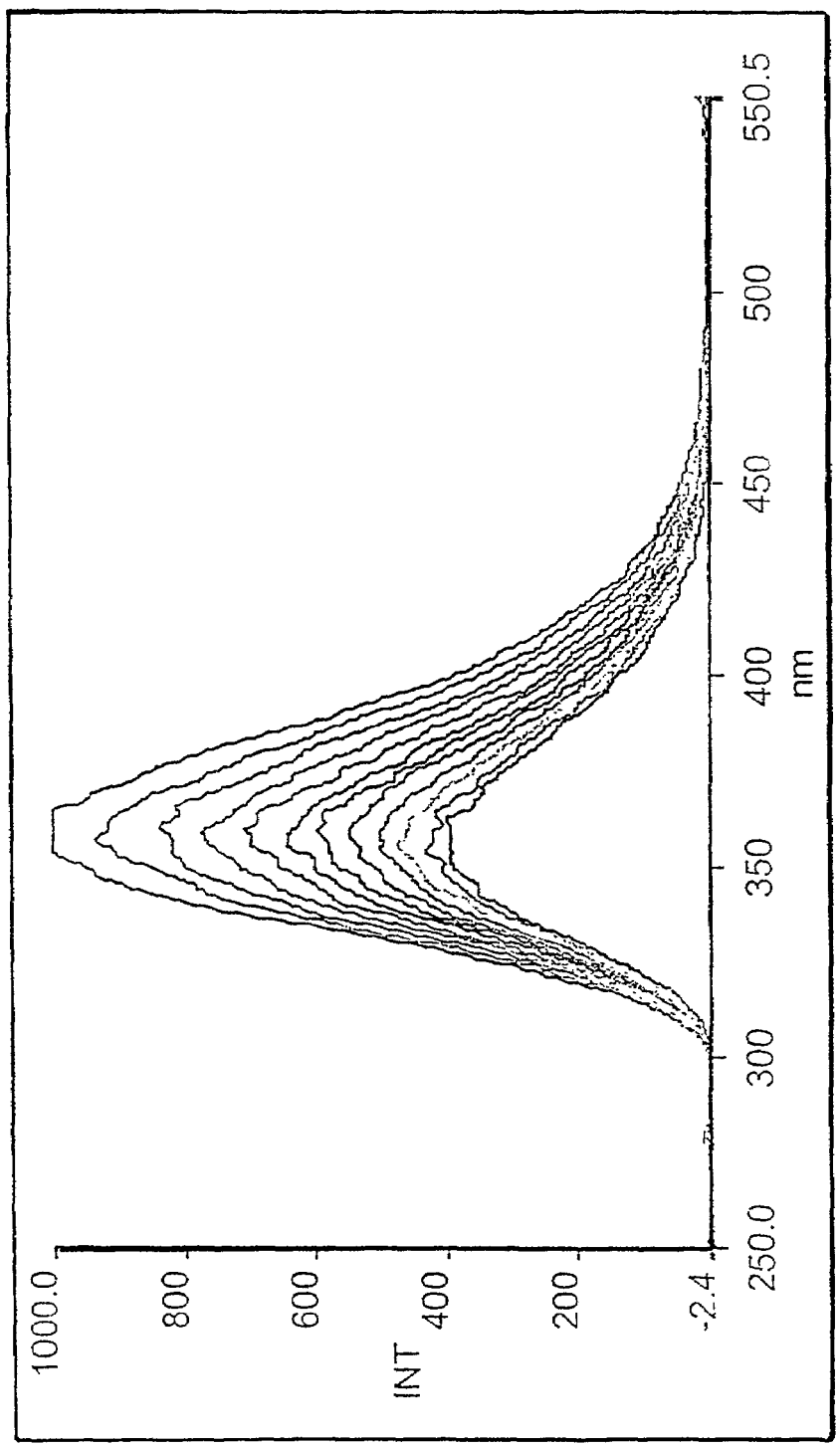

FIG. 7h is a graph illustrating binding to a peptide sequence VCDWWGWGIC. In the graph, the uppermost trace indicates the peptide VCDWWGWGIC 10-mer (49.1 µM, 2.9 ml) in 0.1 M Tris pH 7.5, excited at 280 m without doxorubicin (the degree of quenching is normalised at 999.99). Titration of doxorubicin at stoichiometric ratio of the peptide:doxorubicin is shown in sequence from the second to top trace to the bottom trace as follows:—1:0.1 (917.99); 1:0.2 (835.53); 1:0.3 (769.34); 1:0.4 (704.25); 1:0.5 (633.91); 1:0.6 (594.31); 1:0.7 (547.73); 1:0.8 (498.54); 1:0.9 (457.70); 1:1 (415.96); 1:1.1 (390.24). The number in brackets, following each titration, is the relative intensity of the peak at 359.25 nm, indicating the degree of quenching.

Binding of other xenobiotic compounds (typically planar aromatic hydrocarbons) to the binding site of aromatic hydrocarbon receptors may be similarly measured. Alternatively, the binding of fluorescent compounds (e.g. doxorubicin) may be measured by their quenching on binding to such sites by quenching moieties present at those sites. Similarly, where the binding moiety is neither a quencher or fluorophore, the binding moiety may be attached to a fluorophore or quencher, such that the modified binding agent competes with another binding agent so producing a measurable signal according to this invention. For example the latter configuration may be used to measure binding of a ligand to an antibody. It will be understood by those skilled in the art that measurement of binding to a range of ligands or substrates to proteins and enzymes can be achieved similarly according to this invention.

Various distances of proximity of a fluorophore and quenching moiety may be achieved using peptide structures. This may be as simple as forming cysteine analogues of the fluorophores and bringing the pairs of fluorophores (or fluorophore-quenching moieties) into close proximity on formation of a cystine disulphide bridge. Polyglutamic acid oligopeptides can also be used, attaching the interacting moieties to the side chains at the desired distances. Repeating units of N5-(2-hydroxylethyl)-L-glutamine residues with n between 3 and 9 can also be used to separate interacting units on a polypeptide chain which is flexible in fluid solvents, providing variable end to end distances as the chain relaxes in the fluid. Alternatively, rigid helical structures may be formed using (L-proline)$_n$ residues, separating interacting structures by 1.2 nm (n=1) to 4.6 nm (n=2). The fluorophores or quenching moieties may be attached to such backbones via various lengths of spacer chains, typically hydrocarbons of lengths C4 to C16. Saturated hydrocarbons form flexible chains, whereas increased rigidity and/or orientations can be achieved by the use of cis and trans unsaturated chains. Side groups on the hydrocarbon backbone may be used to create relative degrees of bonding or steric hindrance or between the chains (for example, aromatic, carboxyl, amino, nitro, chloro).

Figure 8:
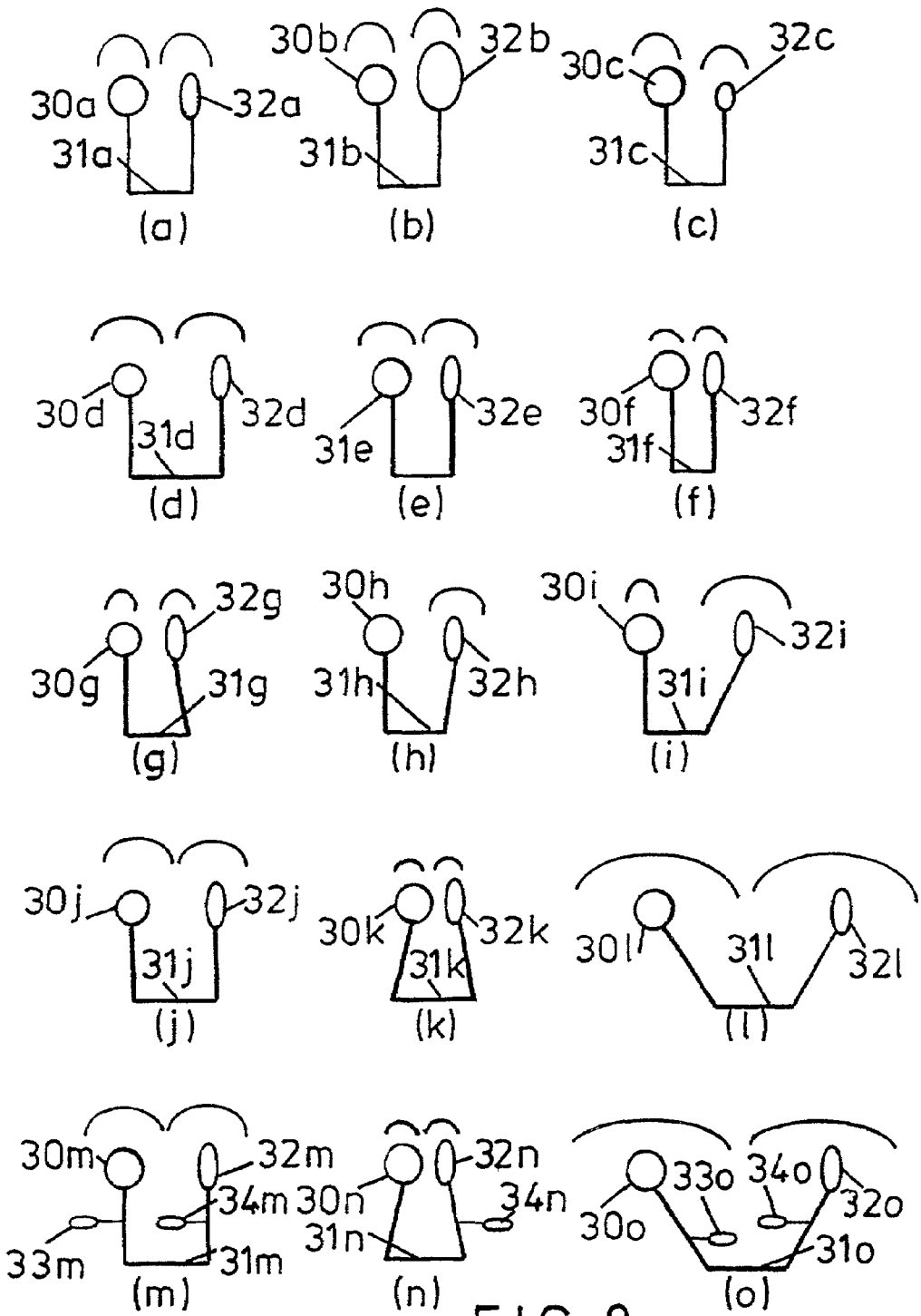
FIG. 8 is a schematic illustration of various configurations of active species.
Figure 9:
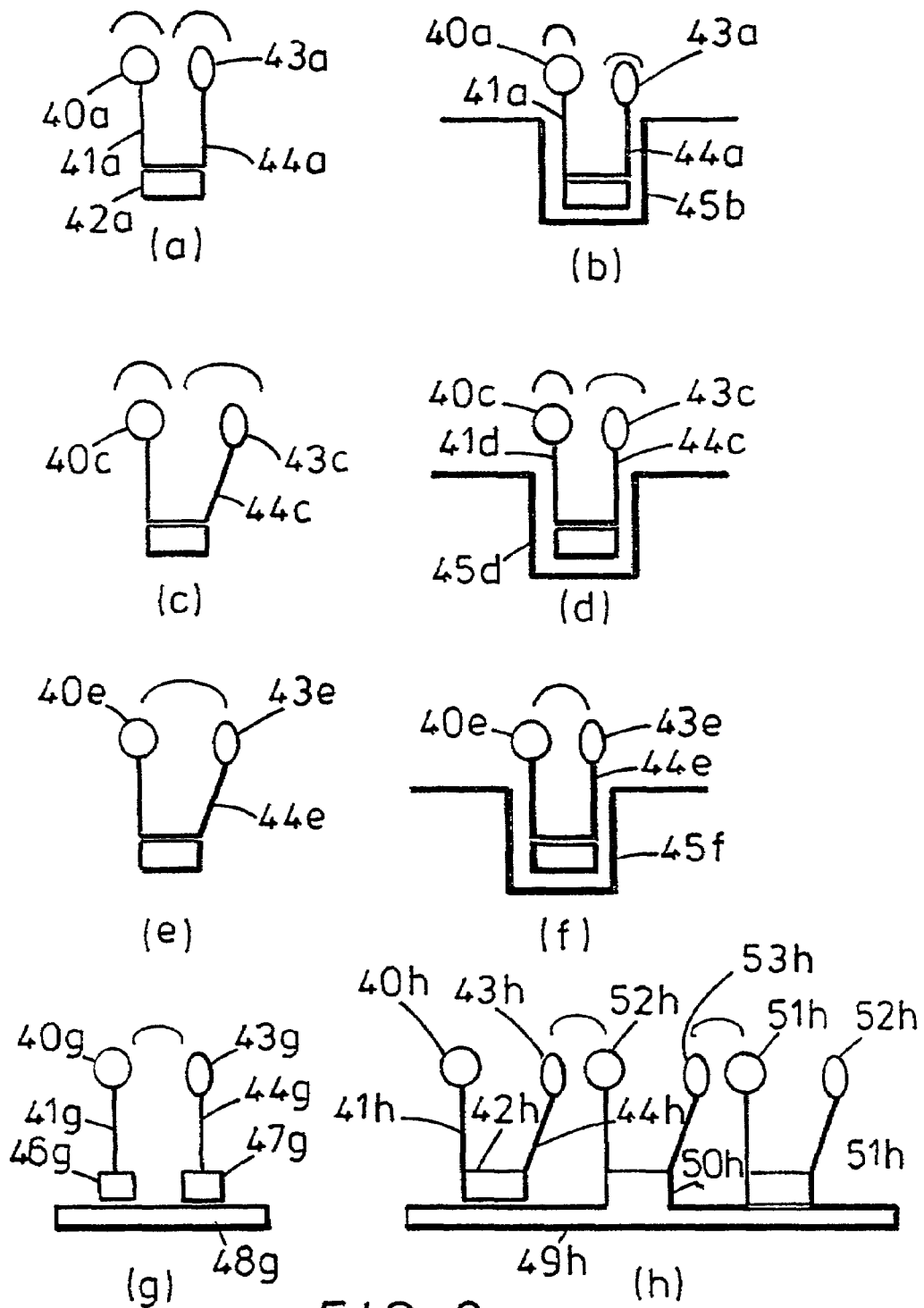
FIG. 9 is a schematic illustration of various configurations of active species.

The fluorophores and quenching moieties mentioned above, together with the structural frameworks mentioned above may also be used to construct the configurations illustrated in FIGS. 8 and 9.

FIG. 8 illustrates a second method via which the period between successive interactions between a fluorophore and a quenching moiety may be modified. Referring to FIG. 8a, a fluorophore 30a is attached by a semi-flexible spacer molecule 31a. A quenching moiety 32a is attached to an opposite end of the spacer molecule 31a. The fluorophore 30a and quenching moiety 32a move periodically closer to and away from each other as the spacer arm 31a flexes. Quenching, either static quenching or collision quenching, will occur when the fluorophore 30a and quenching moiety 32a are sufficiently close.

In FIGS. 8(a)–(c) a fluorophore 30a–c is shown adjacent to three different quenching moieties respectively 32a–c. In each case, the fluorophore 30a–c and quencher moiety 32a–c have spacer arms of the same length. However, the quenching moieties 32 themselves have different properties.

For example in the case of static quenching, the characteristic period during which the fluorophore and the quenching moiety form a complex may be altered by using a different quenching moiety.

In FIGS. 8(d)–(f) the fluorophore 30d–f is separated from the quencher moiety 32d–f by spacer molecules 31d–f of different lengths. As the length of the spacer molecules 31d–f is reduced, the time between successive interactions between the fluorophore 30d–f and the quenching moiety 32d–f is correspondingly reduced.

In FIGS. 8(g)–(i) the flexibility of that part of the spacer molecule 31g–i upon which the quenching moiety 32g–i is varied, affecting the quenching action of the quenching moiety 32g–i. As the flexibility of the spacer molecules 31d–f is increased, the time between successive interactions between the fluorophore 30d–f and the quenching moiety 32d–f is correspondingly increased. Where the flexibility of the spacer molecule is low, for example as shown in FIG. 8g, the spacer molecule 31 g may be configured to ensure that the fluorophore 30d–f and the quenching moiety 32d–f approach each other sufficiently closely to interact as required. The conformation of the spacer molecule (i.e. its configuration at rest) may also be altered.

In FIGS. 8(j)–(l), both the length and the flexibility of the spacer arms 31j–l are varied. In FIG. 8j the fluorophore 30j and quencher moiety 32j are held an intermediate distance apart, and have an intermediate flexibility, as illustrated by the length of the curves located above the fluorophore 30j and quencher moiety 32j. In contrast to this, in FIG. 8k the fluorophore 30k and quencher moiety 32k are held closer together with a greater rigidity. This modification of the separation and movement of the fluorophore 30k and quencher moiety 32k provides will reduce the period between successive interactions between the fluorophore 30k and quenching moiety 32k. FIG. 8l shows a fluorophore 30l and quencher moiety 32l held at a greater separation and with more flexibility than that shown in FIG. 8j. This will increase the period between successive interactions between the fluorophore 30l and quenching moiety 32l.

In FIGS. 8(m)–(o) further moieties 33m,o,34m–o are provided on the spacer molecules 31m–o. The effect of the further moieties is dependent upon their properties, which are well known in the art, for example including steric hindrance.

Upon binding to a target molecule, an interaction between a fluorophore and a quenching moiety may be influenced by interaction between the binding site and either or both of the fluorophore and the quenching moiety.

In FIG. 9 it is shown how the interaction between a fluorophore, which is attached by a spacer molecule to a binding moiety, is altered by becoming attached to a molecular binding site. By reference to the above as a typical example, tryptophan and a xenobiotic quencher (e.g. a drug) may be so pre-assembled with suitable spacer, such that on binding of the drug moiety to a xenobiotic (e.g. a drug) binding site, the constrainment of the probe assembly or active species on binding would be altered so as to produce a different quenching period compared to the unbound assembly. In this way the proportion of unbound and bound assembly may be measured.

Referring first to FIG. 9a, in the above case and in the general case, a fluorophore 40a is attached via a first flexible spacer molecule 41a to a binding moiety 42a. A quenching moiety 43a is attached via a second flexible spacer molecule 44a to the binding moiety 42a. The fluorophore 40a and the quenching moiety 43a both move in a periodic manner, due to the flexibility of the spacer molecules 41a, 44a.

The entire assembly shown in FIG. 9a may be considered to be a probe. FIG. 9b shows the probe 40a–44a located at a binding site in a target molecule 45b. The target molecule interacts with the quenching moiety 43a, modifying its properties. For example, in the case of static quenching, the period over which the fluorophore 40a remains attached to the quenching moiety 43a may be modified by the binding site 45b.

FIGS. 9c–d represent an arrangement whereby a fluorophore 40c attached to a first spacer molecule 41d interacts with a binding site 45d, thereby modifying the properties of the fluorophore. The modification may simply be a change of the energy or lifetimes of some of the energy levels of the fluorophore (levels 14–18 in FIG. 6).

FIGS. 9c–f illustrate how the range of movement of a quenching moiety 43c,e attached to a second spacer molecule 44c,e may be affected by the binding site 45d,f. In the illustrated examples the period between successive interactions between the fluorophore 40c,e and the quenching moiety 43c,e is reduced.

FIG. 9g shows a fluorophore 40g attached by a first spacer molecule 41g to a first binding moiety 46g, and a quenching moiety 43g attached by a second spacer molecule 44g to a second binding moiety 47g. A target molecule 48g is provided with first and second binding sites which are spaced apart such that when the binding moieties 46g, 47g are located at the binding sites, the fluorophore 40g and quenching moiety 43g are at a predetermined separation. Changing the spacing of the binding sites will alter the period between successive interactions between the fluorophore 40g and the quenching moiety 43g.

In FIG. 9h a first probe comprises a fluorophore 40h attached via a first flexible spacer molecule 41h to a binding moiety 42h, and a quenching moiety 43h attached via a second flexible spacer molecule 44h to the binding moiety 42h. The binding moiety 42h of the first probe is arranged to locate at a first a binding site in a target molecule 49h. Second and third probes having a similar configuration to the first probe are provided with different binding moieties 50h,51h arranged to locate at second and third binding sites in the target molecule 49h. The first quenching moiety 43h will interact periodically with a fluorophore 52h comprising part of the second probe. A second quenching moiety 53h comprising part of the second probe will interact with a third fluorophore comprising part of the third probe. In this manner the three probes shown in FIG. 9h will provide a fluorescence output which is dependent upon each of the three probes locating at their respective binding sites. This approach is useful in sequencing, where signatures corresponding to the components assembled may be arranged to provide a signal indicating the location and types of their neighbours.

The assemblies shown in FIGS. 9g,h may provide means to identify which residues have been assembled next to each other in a combinatorial synthesis. In the prior art these have to be separated and analysed, whereas using the invention the proximity of residues labelled with different fluorophores and quenchers may be identified.

Fluorescence Resonant Energy Transfer (FRET) refers to a configuration of two fluorophores such that the energy of a first of the fluorophores (the donor) is absorbed by a second of the fluorophores (the acceptor). The mechanism via which the energy transfer takes place is primarily a result of dipole—dipole interactions, so-called radiationless energy transfer, not involving the appearance of a photon, although radiation-based transfer may also be measured according to the invention. In order for the transfer to be resonant the energy of the acceptor should be slightly less than the energy of the donor. That is, the rate of energy transfer depends on the extent of overlap of the emission spectrum of the donor and the absorption spectrum of the acceptor. In the terminology used in this description, the active species is the two fluorophores when they are sufficiently close for FRET to occur. In other words, the energy levels shown in FIG. 6 describe the two fluorophores only when they are sufficiently close for FRET to occur.

The two fluorophores comprising a FRET active species may be arranged to come together periodically by attaching them to a suitably configured spacer molecule. An example of such a configuration is shown in FIG. 10a, where a first fluorophore 60a and a second fluorophore 61a are separated by a spacer molecule 62a, and are configured to oscillate such that they periodically approach sufficiently close for FRET to occur.

The invention allows measurement of the period during which the fluorophores are sufficiently close for FRET to occur (several photons may be emitted by the active species during this period if the cycle time of the active species is fast enough). No photons will be emitted from the active species when the fluorophores are spaced apart (the FRET active species does not exist at that time). The time during which photons are emitted from the active species and the time during which no photons are emitted from the active species will be seen as two separate components of data acquired using the invention.

In contrast to the invention, prior art fluorescence measurement methods are not capable of monitoring the cycle described above. FRET will only be seen if the fluorophores are sufficiently close together when excitation occurs. The prior art methods are not capable of determining the period between successive formations of a FRET active species by two fluorophores.

Each fluorophore may absorb and emit photons as an active species in its own right when the fluorophores are spaced apart. Where measurements are made using the invention these photons may be recognised from their separation (i.e. the characteristic cycle times of the fluorophores).

Figure 10:
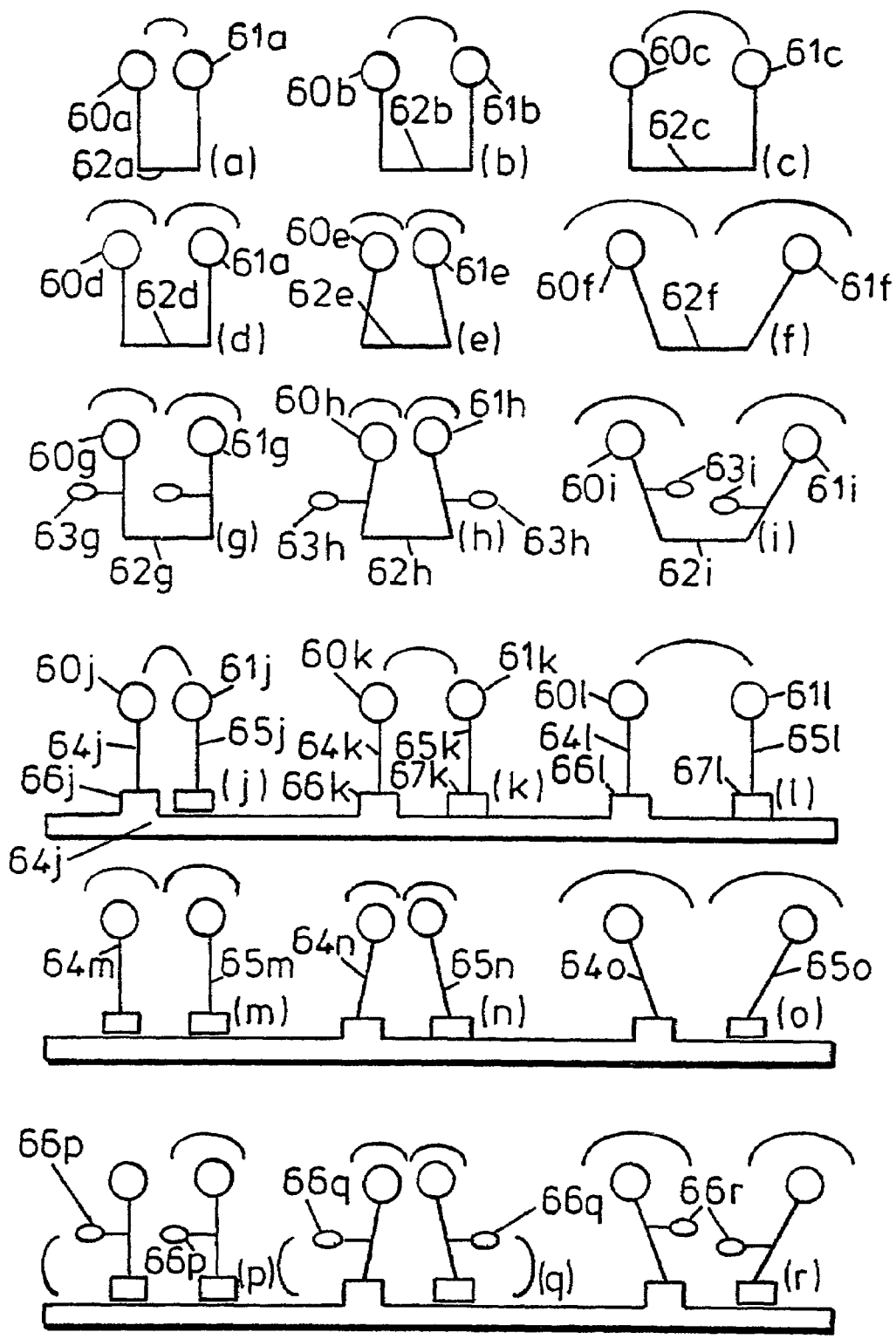
FIG. 10 is a schematic illustration of various configurations of active species.

FIG. 10 illustrates several arrangements via which the time elapsed between successive formations of a FRET active species by two fluorophores may be modified. In FIGS. 10a–c the length of the spacer molecule 62a–c connecting the two fluorophores 60a–c,61a–c is modified. This will change the period between successive formations of the active species; a longer spacer molecule 62a–c providing a longer period.

The flexibility of the spacer molecule may also be modified, as shown in FIGS. 10d–f. Again, this will change the period between successive formations of the active species; a more flexible spacer molecule 62d–f providing a longer period.

In FIGS. 10g–i modifying moieties 63g–h are added to the spacer molecule 62g–i. Again, this will have an effect on the period between successive formations of the active species, the effect being determined by the properties of the modifying moiety 63g–h.

Two fluorophores may be provided with binding moieties, each binding moiety being configured to bond to a predetermined binding site in a predetermined molecule. In this case, the two binding sites are located at a predetermined separation which is chosen such that the two fluorophores will be separated by a distance which provides a FRET active species having desired properties. For example, in FIGS. 10j–l first and second fluorophores 60j,61j are attached via first and second spacer molecules 64j,65j to first and second binding moieties 66j,67j. The binding moieties are arranged to locate at binding sites in a target molecule 68j with a separation which provides a FRET active species having desired properties.

In FIGS. 10k,l the separation of the binding sites is increased, resulting in a corresponding increase of the period between successive formations of the FRET active species. FIGS. 10 m–o illustrate changes of the flexibility of the spacer molecules 64m–o,65m–o upon which the fluorophores are held. FIGS. 10p–r illustrate the effect of adding modifying moieties 66p–r to the spacer molecules.

Turning now to FIG. 11a, a FRET active species is formed by first and second fluorophores 70a, 71a. Each of the fluorophores is attached via a spacer molecule 72a, 73a to a binding moiety 74a, 75a. Each binding moiety 74a, 75a is also provided with a quenching moiety 76a, 77a attached via a spacer molecule 78a, 79a to the binding moiety 74a, 75a. The binding moieties are arranged to bind to binding sites in a target molecule 80a which are spaced apart such that fluorophores 71a, 72a will periodically form a FRET active species having desired properties. The quenching moieties 76a, 77a are chosen to modify the interaction resulting in the formation of the FRET active species.

A typical example using FRET would be to couple or label 5-[2-(iodoacetyl)aminoethyl]-5-aminonapthalene-1-sulphonic acid (1,5 IAEDANS) and iodoacetamidefluorescein to protein molecules to investigate changes in distance of separation on changes of conformation of the protein, or regiospecifically to a peptide chain of different lengths (for example using the above proline structure to obtain defined distances of separation) to obtain different separations. A further example, indicated by FIGS. 10j–r, would be to bind donor and acceptor fluorophores via DNA probes to adjacent positions to complimentary regions on single stranded DNA, according to well know procedures, often referred to as a split DNA probe. The degree of adjacent binding and complimentarity of the split probe and target DNA may be then be measured according to the invention.

FIG. 11b corresponds to FIG. 11a, except that only one of the fluorophores 70b, 71b is provided with a quenching moiety 77b.

FIG. 11c corresponds to FIG. 11b, except that the target molecule 80c is arranged to constrain movement of the fluorophores 70c, 71c and the quenching moiety 77c.

In FIG. 12a a FRET active species is formed by first and second fluorophores 90a, 91a. Each of the fluorophores is attached via a spacer molecule 92a, 93a to a binding moiety 94a, 95a. The binding moieties are arranged to bind to binding sites in a target molecule 96a a which are spaced apart such that fluorophores 91a, 92a will periodically form a FRET active species having desired properties. The shape of the target molecule 96a is such that the first and second fluorophores 90a, 91a interact with the target molecule 96a, modifying the properties of the FRET active species. In FIG. 12a, the period between successive formations of the FRET active species will be changed by the interaction with the target molecule 96a.

FIG. 12b corresponds to FIG. 12a except that a modifying moiety 97b is attached to one of the spacer molecules 92b. The modifying moiety 97b interacts with the target molecule 96b, and reduces the period of movement of the spacer molecule 92b. The period between successive formations of the FRET active species is correspondingly reduced.

FIG. 12c corresponds to FIG. 12b except that a modifying moiety 97c, 98c is attached to each of the spacer molecules 92c, 93c. The modifying moieties 97c, 98c interact with the target molecule 96c, and reduce the period of movement of the spacer molecules 92c, 93c. The period between successive formations of the FRET active species is correspondingly reduced.

Typical examples of donor-acceptor pairs are as follows: fluorescein-teramethylrhodamine, IAEDANS-fluorescein, and EDANS-DABCYL. These and other donor-acceptor pairs are available from Molecular Probes Inc., 4849 Pitchford Avenue, Oreg., 97402-9165 USA, and are described in the catalogue issued by that company. The above structures may be made using known donor-acceptor pairs, together with the structural frameworks mentioned above.

The formation of excimer or exciplex structures between one or more moieties to provide a fluorophore is known in the art, for example pyrene dimers and pyrene-DMA. The molecules which combine to form an excimer/exciplex structure may be fluorophores in their own right. Where this is the case, the formation of an excimer or an exciplex results in a red-shift (Stokes-shift) of the emitted fluorescent light (as is seen for fluorescent resonant energy transfer (FRET)). Excimers and exciplexes commonly exhibit more specificity than FRET molecules when they are used as biological probes. As with other fluorescent materials, the characteristic lifetimes of excimers and exciplexes are generally known and can be influenced in the same way, for example, by altering their dielectric environment.

The period between successive interactions between the excimer and exciplex partners may be modified by any of the following methods: altering the length of either or both of the spacer molecules upon which the excimer or exciplex partners are held; altering the flexibility of either or both of the spacer molecules upon which the excimer or exciplex partners are held; modification of the probe or part thereof with hydrophilic, polar, charged or hydrophobic moieties; and modification of one of the excimer or exciplex partner moieties.

The modification of the interaction between the partners in the formation of the excimer or exciplex allows the period between successive interactions to be manipulated. Modification of the interaction may also change the lifetimes of the excimer or exciplex. The period between successive interactions of the excimer or exciplex molecules will also be affected by the binding of the constituent molecules to a target molecule.

Figure 11:
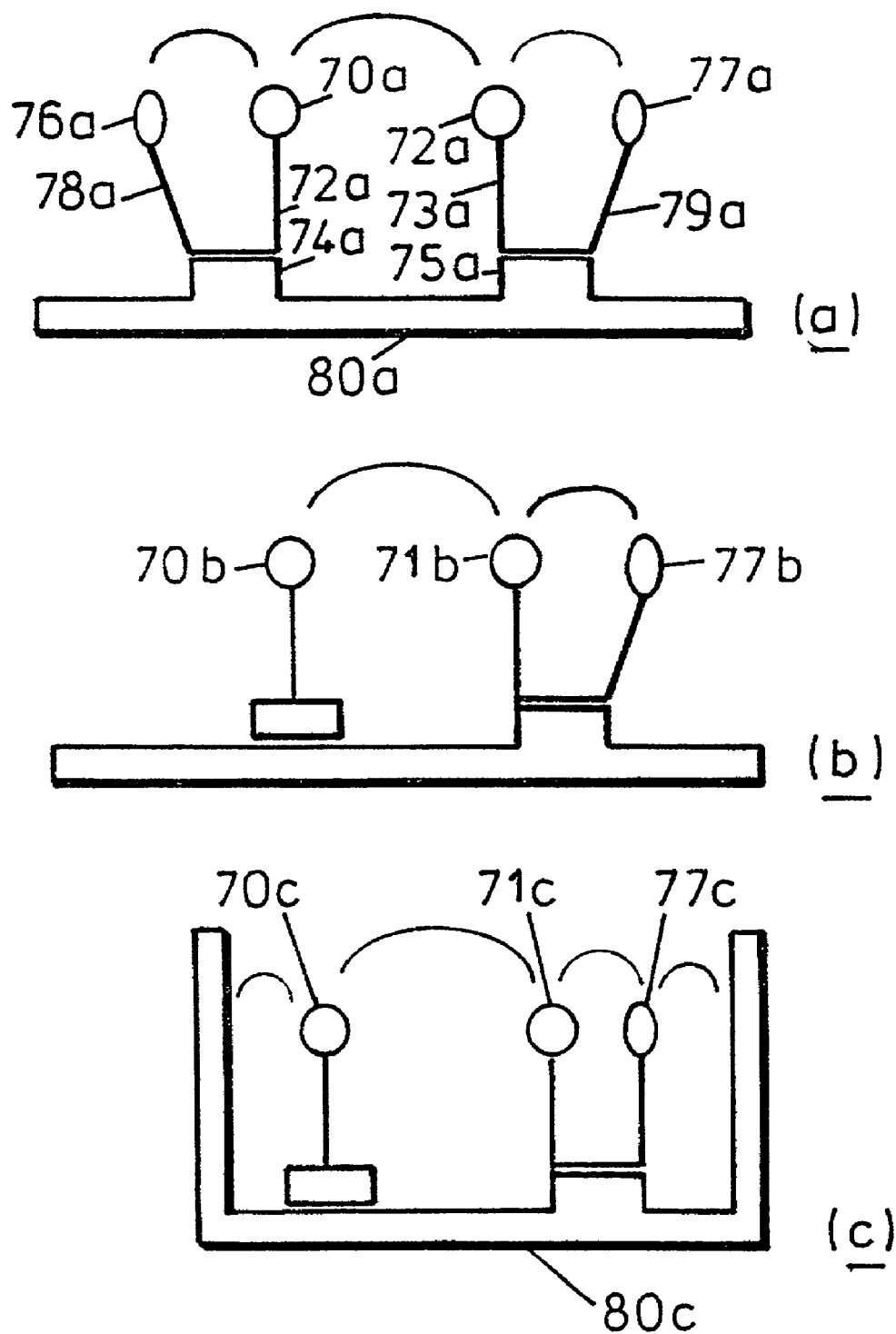
FIG. 11 is a schematic illustration of various configurations of active species.
Figure 12:
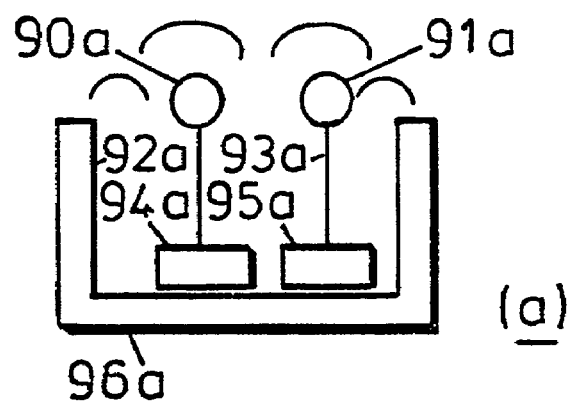
FIG. 12 is a schematic illustration of various configurations of active species.
Figure 12:
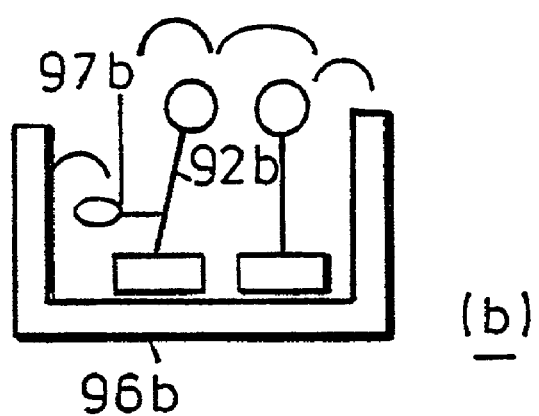
Figure 12:
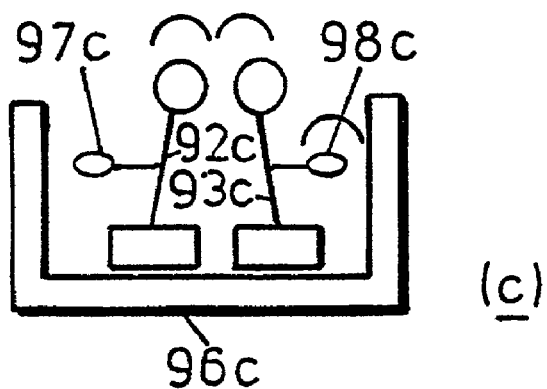

The arrangements illustrated in FIGS. 10 to 12 and described in terms of FRET active species will work in the same way to modify properties of excimers or exciplexes.

Pyrene and perylene and their many derivatives are suitable for assembly into interacting pairs. For example, 1-pyrene-acetic acid and its succinimidyl ester, 1-pyrene butanoic acid, 1-pyrene-butanol, N-(1-pyrene-butanoyl)cysteic acid and its suiccinimidyl ester, 1-pyrenecarboxylic acid, 1-pyrene-decanoic acid, 1-pyrene-hexanoic acid, N-(1-pyrene)-iodoacetamide, N(1-pyrene)maleimide, 1-pyrene-methylamine.

Exciplex pairs may be formed variously from perylene, pyrene, N,N-dimethylaniline, and between thiocyanine and acridine orange.

Although the above description has focussed mainly on fluorescence, the invention may be used to measure phosphorescence or luminescence. The components and structures required to generate and/or modify phosphorescence or luminescence emissions will be apparent to those skilled in the art in the light of the above description.

Although the above description has discussed the generation of fluorescent light from structures which include a fluorophore and a quenching moiety or other moiety arranged to interact with the fluorophore, it will be understood that similar effects may be obtained without said structures via the diffusion of fluorophores and modifying moieties in a solution. In the case of collisional quenching, the volume of fluorophores and the distance they travel between collisions with quenching moieties will affect the measured fluorescence intensity. In the case of fluorophores having long characteristic lifetimes, diffusion may be over considerable distances, generally producing more quenching for a particular quencher concentration and diffusion coefficient. In the case of fluorophores having shorter lifetimes, the same degree of quenching will only be seen if the concentration of quenching moieties is greater or the rate of diffusion is greater.

A fluorophore may be located in a solution containing a buffer arranged to interact with the fluorophore. The active species in this case is effectively the sum of the fluorophore and that part of the buffer with which it is interacting.

It will be understood that the characteristic cycle time of a fluorophore may also be changed by physical modification of a property of the fluorophore, for example by modification of the electromagnetic, magnetic, acoustic or thermal energy. Some of these modifications have been described above. Other suitable modifications will be obvious to those skilled in the art.

The characteristic cycle times of suitable materials may be modified by ultrasonic irradiation. The material must be chosen such that ultrasonic irradiation will modify mechanical and thermo-mechanical interactions within and between them.

An interaction between a fluorophore and a molecule may be achieved by introducing a photo-active group between the fluorophore and the molecule. An example of such a molecule is stilbene. The periodic absorption of energy by such a molecule will modify the characteristic cycle time of fluorescent emission, by creating a localised periodic change in thermal energy and so characteristically polarises the interaction between the fluorophore and the molecule. Similarly, electric fields may be used to modify the interaction between active species according to the invention, for example, as may be achieved by attaching the active species to liquid crystal assemblies.

Although the specific embodiments of the invention described above have referred to continuous excitation of a sample using incident light or a catalyst, the invention is not intended to be limited to these types of excitation, and includes other suitable types of excitation, for example alpha radiation, beta radiation, chemical addition, heat, vibration, an electrical field or a magnetic field. Incident light may be provided by light emitting diodes (LED), super luminescent diodes, thermal lamps or spectral lamps.

Although the specific examples of the invention described above refer to the emission and detection of photons, the invention may be applied to the emission and detection of any suitable quanta, for example, electrons, neutrons or phonons. It may be possible in some applications to set a threshold value via which an analogue signal may be converted into quanta, to allow the invention to be used.

What is claimed is:

1. A method of analysis for determining a characteristic cycle time of a sample, the method comprising:

exciting active elements in the sample with sufficient intensity and duration that at least some of the active elements are re-excited to an excited state substantially immediately following relaxation to a ground state, detecting quanta emitted by the active elements in the sample to obtain a detected signal, and analyzing the detected signal to derive the characteristic cycle time, wherein the number of active elements in the sample and the intensity of the excitation are such that quanta are detected in a stream in which individual quanta are distinguishable from each other.

2. A method according to claim 1, wherein the analysis of the detected signal includes auto correlation of the detected signal.

3. A method according to claim 1, wherein the characteristic cycle time of the sample is modified by chemical or physical modification of the active elements' environment, and the modified characteristic cycle time is determined.

4. A method according to claim 1, wherein:

at least some of the active elements have an excited level, an upper level of an emission transition and a lower level of the emission transmission, and emit a detectable quanta upon relaxation from the upper level of the emission transition to the lower level of the emission transition, the lifetime of the lower level of the emission transition or another energy level having a lesser energy than the lower level of the emission transition is influenced by modification of the active elements' environment, and the effect of such modification is determined.

5. A method according to claim 4, wherein:

at least some of the active elements are bound to a substrate by a member that permits vibrational motion of the active element wherein the lifetime of the lower level of the emission transition or another energy leel having a lesser energy than the lower level of the emission transition, is altered by modifying the electronic environment of the active element.

6. A method according to claim 5, wherein:

the modification of the electronic environment is effected by the presence of at least one modifying moiety which influences the electronic environment of the active element.

7. A method according to claim 6, wherein:

a change in cycle time is caused by transfer to energy to the modifying moiety from the lower level of the emission transition or another energy level having a lesser energy than the lower level of the emission.

8. A method according to claim 3, wherein:

the cycle time is modified by changes in conformation of the active element relative to a modifying moiety.

9. A method according to claim 3, wherein:

each active element comprises part of a probe, whereby the probe is moved between different dielectric environments, including those occurring in a molecule or its solvent, the characteristic cycle time of the probe is affected by time scales of the motion of the active element between different dielectric environments, and the motion is affected by modifications including at least one of the following:

(e) altering the size of the probe;

(f) altering the distance between the active element and the remainder of the probe;

(g) altering the rigidity of a spacer molecule between the active element and the remainder of the probe; or (h) modifying the probe or part thereof with hydrophilic, polar, charged or hydrophobic moieties.

10. A method according to claim 3, wherein:

the active element comprises part of a species which periodically interacts with a modifying moiety, and the periods during which the species interacts with the modifying moiety and the periods during which the species does not interact with the modifying moiety are measures.

11. A method according to claim 3, wherein:

the active element comprises part of a species which periodically interacts with a quenching moiety and is thereby quenched by a static quenching mechanism, and the periods during which the species is active and the periods during which the species is inactive are measured.

12. A method according to claim 3, wherein:

the active element comprises part of a species which periodically interacts with a quenching moiety and is thereby quenched by a collisional quenching mechanism, and the periods during which the species is active and the periods during which the species is inactive are measured.

13. A method according to claim 11, wherein the period of the periodical interaction is influenced by modification of a property of the species or the modifying moiety or quenching moiety.

14. A method according to claim 13, wherein the modification comprises changing the length of a spacer molecule upon which the active element is located, or the length of the spacer molecule upon which the modifying moiety or quenching moiety is located.

15. A method according to claim 13, wherein the modification comprises changing the flexibility of a spacer molecule upon which the active element is located, or the flexibility of the spacer molecule upon which the modifying moiety or quenching moiety is located.

16. A method according to claim 13, wherein the modification comprises adding a modifying moiety to a spacer molecule upon which the active element is located, or to a spacer molecule upon which the modifying moiety or quenching moiety is located.

17. A method according to claim 13, wherein:

the active element is attached via a spacer molecule to a binding site, and the modification results from an interaction with the binding site.

18. A method according to claim 13, wherein:

the modification results from a restriction of periodic movement of the spacer molecule upon which the active element is located, or the spacer molecule upon which the modifying moiety or quenching moiety is located.

19. A method according to claim 13, wherein the active element is attached via a spacer molecule to a binding site, and the modification results from an interaction with a modifying moiety attached to the binding site.

20. A method according to claim 13, wherein the active element is attached via a first spacer molecule to a first binding site, and a modifying moiety or quenching moiety is attached via a second spacer molecule to a second binding site, and the separation of the first and second binding sites determines the periodicity of the interaction between the active element and the modifying moiety or quenching moiety.

21. A method according to claim 3, wherein first and second elements which periodically interact to form the active element, and the period during which the first and second elements interact to form the active element and the periods during which the first and second elements do not interact to form the active element are measured.

22. A method according to claim 21, wherein
the active element is a fluorescence resonant energy transfer species.

23. A method according to claim 21, wherein the active element is an excimer or an exciplex.

24. A method according to claim 1, wherein
an excitation cross section of a ground state of an active element is varied periodically, and
the period of variation is measured.

25. A method according to claim 1, wherein:
the active element emits fluorescence photons which interact with a solution in which the active elements are held, and
the effect of the solution is monitored by modulating properties of the solution.

26. A method according to claim 1 further comprising
exciting the active elements using an excitation pulse and determining the time elapsed between excitation and the emission of a quanta from the active element, and
subtracting that elapsed time from the characteristic cycle time.

27. A method according to claim 1, wherein
excitation of active element in the sample is by a chemical reaction.

28. A method according to claim 1, wherein the active elements have an upper excited state, a lower excited state and a ground state, and emit a detectable quanta upon relaxation from the upper excited state to the lower excited state, the method further comprising:
exciting second elements to an excited state such that the second elements transfer excitation energy to the active elements, thereby exciting the active elements to the upper excited state.

29. An analysis apparatus for determining the characteristic cycle time of active elements in a sample, said apparatus comprising:
means for exciting active elements in the sample with sufficient intensity and duration that at least some of the active elements are re-excited to an excited state substantially immediately following relaxation to a ground state,
means for detecting quanta emitted by the sample to obtain a detected signal,
analyzing means for analyzing the detected signal to derive the characteristic cycle time,
wherein the number of active elements in the sample and the intensity of the excitation are such that quanta are detected in a stream in which individual quanta are distinguishable from each other.

* * * * *

UNITED STATES PATENT AND TRADEMARK OFFICE
CERTIFICATE OF CORRECTION

| | | |
|---|---|---|
| PATENT NO. | : 7,098,039 B1 | Page 1 of 1 |
| APPLICATION NO. | : 09/743195 | |
| DATED | : August 29, 2006 | |
| INVENTOR(S) | : Christopher J. Lloyd et al. | |

It is certified that error appears in the above-identified patent and that said Letters Patent is hereby corrected as shown below:

On the title page under (73) Assignee, delete "The Victoria University of Manchester" and substitute therefor -- The University of Manchester --.

Signed and Sealed this

Twenty-fourth Day of November, 2009

David J. Kappos
*Director of the United States Patent and Trademark Office*